(12) United States Patent
Davis et al.

(10) Patent No.: US 7,750,030 B2
(45) Date of Patent: Jul. 6, 2010

(54) ACUTE PHARMACOLOGIC AUGMENTATION OF PSYCHOTHERAPY WITH ENHANCERS OF LEARNING OR CONDITIONING

(76) Inventors: Michael Davis, 5570 Oakwood Dr., Stone Mountain, GA (US) 30087; Kerry J. Ressler, 1792 Hickory Rd., Chamblee, GA (US) 30341

( * ) Notice: Subject to any disclaimer, the term of this patent is extended or adjusted under 35 U.S.C. 154(b) by 736 days.

(21) Appl. No.: 10/473,640

(22) PCT Filed: Mar. 28, 2002

(86) PCT No.: PCT/US02/09467

§ 371 (c)(1),
(2), (4) Date: Apr. 22, 2004

(87) PCT Pub. No.: WO02/078629

PCT Pub. Date: Oct. 10, 2002

(65) Prior Publication Data

US 2004/0208923 A1   Oct. 21, 2004

(51) Int. Cl.
*A61K 31/42* (2006.01)
*A01N 43/80* (2006.01)
*A01N 43/82* (2006.01)
*A01N 43/64* (2006.01)
*A01N 43/02* (2006.01)

(52) U.S. Cl. .................. 514/380; 514/378; 514/360; 514/359; 514/449

(58) Field of Classification Search .................. 514/376, 514/561, 380, 378, 360, 354, 449
See application file for complete search history.

(56) References Cited

U.S. PATENT DOCUMENTS

| | | | |
|---|---|---|---|
| 4,904,681 A | | 2/1990 | Cordi |
| 5,061,721 A | * | 10/1991 | Cordi et al. .................. 514/376 |
| 5,086,072 A | | 2/1992 | Trullas et al. |
| 5,087,633 A | | 2/1992 | Cordi |
| 5,187,171 A | | 2/1993 | Cordi |
| 5,260,324 A | | 11/1993 | Cordi |
| 5,428,069 A | | 6/1995 | Skolnick |
| 5,468,763 A | | 11/1995 | Cordi |
| 5,523,323 A | | 6/1996 | Maccecchini |
| 6,028,070 A | | 2/2000 | Heiligenstein |
| 6,184,222 B1 | | 2/2001 | Heiligenstein |
| 6,228,875 B1 | | 5/2001 | Tsai |
| 6,333,357 B1 | | 12/2001 | Elg |
| 6,355,681 B2 | | 3/2002 | Javitt |
| 6,391,922 B1 | * | 5/2002 | Fogel .................. 514/702 |
| 6,420,351 B1 | | 7/2002 | Tsai |
| 6,656,962 B2 | | 12/2003 | Herting |
| 6,667,297 B2 | | 12/2003 | Tsai |
| 6,699,682 B2 | | 3/2004 | Gilula et al. |
| 6,943,166 B1 | | 9/2005 | Pullman et al. |
| 6,974,821 B2 | | 12/2005 | Tsai |
| 2001/0027204 A1 | | 10/2001 | Herting |
| 2002/0156112 A1 | | 10/2002 | Bamdad |
| 2002/0183372 A1 | | 12/2002 | Herting |
| 2002/0183373 A1 | | 12/2002 | Herting |
| 2002/0188009 A1 | | 12/2002 | Sit et al. |
| 2003/0073730 A1 | | 4/2003 | Fakouhi |
| 2003/0092734 A1 | | 5/2003 | Boger |
| 2004/0048907 A1 | | 3/2004 | Aquila et al. |
| 2004/0127518 A1 | | 7/2004 | Piomelli et al. |
| 2004/0214873 A1 | | 10/2004 | Herting |
| 2005/0014784 A1 | | 1/2005 | Shendelman |
| 2005/0096396 A1 | | 5/2005 | Davis |
| 2005/0131032 A1 | | 6/2005 | Sit et al. |
| 2005/0143314 A1 | | 6/2005 | Patrick et al. |
| 2006/0084659 A1 | | 4/2006 | Davis et al. |

FOREIGN PATENT DOCUMENTS

| | | |
|---|---|---|
| EP | 0238245 B1 | 6/1990 |
| EP | 0432039 A2 | 6/1991 |
| EP | 0378134 A3 | 7/1991 |
| EP | 0319824 B1 | 10/1991 |
| EP | 0387867 B1 | 5/1993 |
| EP | 0525588 A2 | 6/1997 |
| EP | 1084704 A1 | 3/2001 |
| EP | 01444979 A1 | 8/2004 |
| WO | WO/89/05144 A1 | 6/1989 |

(Continued)

OTHER PUBLICATIONS

National Lib. of Medicine, "Anxiety"-2007 Mesh.*

(Continued)

*Primary Examiner*—Frederick Krass
*Assistant Examiner*—Sean Basquill
(74) *Attorney, Agent, or Firm*—Jason P. McDevitt

(57) ABSTRACT

Methods for treating an individual with a psychiatric order with a pharmacologic agent that enhances learning or conditioning in combination with a session of psychotherapy are provided. These methods of the invention encompass a variety of methods of psychotherapy, and psychodynamically oriented psychotherapy, and psychiatric orders including fear and anxiety disorders, addictive disorders, addictive disorders including substance-abuse disorders, and mood disorders. The pharmacologic agents used for the methods of the present invention are ones that generally enhance learning or conditioning, including those that increase the level of norepinephrine in the brain, those that increase the level of acetylcholine in the brain, and those that enhance N-methyl-D-aspartate (NMDA) receptor transmission in the brain.

16 Claims, 8 Drawing Sheets

FOREIGN PATENT DOCUMENTS

| WO | WO96/11698 | * | 4/1996 |
|---|---|---|---|
| WO | WO/96/15787 A1 | | 5/1996 |
| WO | WO/96/15788 A1 | | 5/1996 |
| WO | WO/99/52519 A2 | | 10/1999 |
| WO | WO/99/63989 A1 | | 12/1999 |
| WO | WO/02/39999 A3 | | 5/2002 |
| WO | WO/02/078629 A2 | | 10/2002 |
| WO | WO/2005/016319 A2 | | 2/2005 |

OTHER PUBLICATIONS

Anthony et al , "Anxiolytic -like effects pof NoMethyl-D-aspartate- . . . ", European Journal of Pharmacolgy (abstract only) , 1993 vol. 250(2), pp. 317-324.*
Klodzinska et al., Anticonflict effect of the glycine B receptor partial agonis . . . , (abstract only) , Psychopharmacology(Berl), 2000, vol. 152(2), pp. 224-228.*
Mental Health: A report of the Surgeon General-Chapter 4, Adults and Mental Health.*
Keller et al., A comparisong of nefazodone, the congnitive . . . , The New england Journal of Medicine, 2001, vol. 342:1462-1470.*
David Quartermain, et al, Acute But Not Chronic Activation of the NMDA-Coupled Glycine Receptor With D-cycloserine Facilitates Learning and Retention, 257 Eur. J. Pharmacol. 7 (1994).*
William Falls, et al, Extinction of Fear-Potentiated Startle: Blockade by Infusion of an NMDA Antagonist Into the Amygdala, 12 J. Neurosci. 854 (Mar. 1992).*
Barbara Olasov Rothbaum, et al, Virtual Reality Exposure Therapy for PTSD Vietnam Veterans: A Case Study, 12 J. Traumatic Stress 263 (1999).*
Travis, John, "Fear Not—Scientists are learning how people can unlearn fear," Science News Online, vol. 165, No. 3, Week of Jan. 17, 2004, online.
Goldberg, Carey, "Can drugs help us conquer phobias?" The Boston Globe, Oct. 28, 2003, online.
Ressler, Kerry J. et al., "Regulation of Synaptic Genes during Consolidation of Fear Conditioning," The Journal of Neuroscience, Sep. 15, 2002, vol. 22, No. 18, pp. 7892-7902.
Davis, Michael, et al., "Combining Pharmacotherapy With Cognitive Behavioral Therapy: Traditional and New Approaches," Journal of Traumatic Stress, Oct. 2006, col. 19, No. 5, pp. 571-581.
Barlow, David H. et al., "Cognitive-Behavioral Therapy, Imipramine, or Their Combination for Panic Disorder," JAMA, 2000:283(19), pp. 2529-2536, (Corrections—JAMA, 2000:284(19), p. 2450; JAMA, 2000:284(20), p. 2597).
Davidson, Jonathan R.T. et al., "Fluoxetine, Comprehensive Cognitive Behavioral Therapy, and Placebo in Generalized Social Phobia," Arch Gen Psychiatry, 2004:61, pp. 1005-1013.
Foa, Edna B. et al., "Randomized, Placebo-Controlled Trial of Exposure and Ritual Prevention, Clomipramine, and Their Combination in the Treatment of Obsessive-Compulsive Disorder," Am. J. Psychiatry, 2005:162(1), pp. 151-161.
Marks, Isaac M. et al., "Alprazolam and Exposure Alone and Combined in Panic Disorder with Agoraphobia," British Journal of Psychiatry, 1993:162, pp. 776-787.
Birk, "Pharmacotherapy for Performance Anxiety Disorders . . . ", Journal of Clinical Psychology, (2004) vol. 60(8), p. 867-879.
Bisogno, "Fatty Acid Amide Hydrolase, an Enzyme with many Bioactive Substrates, Possible Therapeutic Implications", Current Pharm Design, (2002) , vol. 8, p. 125-133.
Boje, "Desensitization of the NMDA Receptor Complex by Glycinergic Ligands . . . ", Brain Research, (1993), vol. 603(2), p. 207-214.
Capone, "Drugs that Increase Intelligence?: Application for Childhood Cognitive Impairment", Mental Retardation and Developmental Disabilities Research Reviews (1998), vol. 4, p. 36-49.
Chhatwal, "Enhancing Cannabinoid Neurotransmission Augments the Extinction of Conditioned Fear", Neuropsychopharmacology (2005), vol. 30, p. 516-524.
Davis, "Facilitation of Extinction of Conditioned Fear by D-Cycloserine", American Psychological Society, vol. 14(4), p. 214-219 (2005).
Evins, A. Eden, et al., "D-Cycloserine Added to Risperidone in Patients with Primary Negative Symptoms of Schizophrenia", Schizophrenia Research 56 (2002) p. 19-23.
Gillespie, "Emotional Learning and Glutamate: Translational Perspectives", CNS Spectrums (2005) vol. 10 (10), p. 831-839.
Goff, D., et al. "Augmentation Strategies in the Treatment of Schizophrenia", CNS Spectrums, vol. 6, No. 11, Nov. 2001, p. 904-911.
Heresco-Levy, "N-Methyl-d-Aspartate (NMDA) Receptor-Based Treatment Approaches in Schizophrenia: The First Decade", Int Journal of Neuropsychopharmacology (2000), vol. 3, p. 243-258.
Heresco-Levy, "Placebo-Controlled Trial of D-Cycloserine Added to Conventional . . . ", Am J. Psychiatry (2002), vol. 159(3), p. 480-482.
Heresco-Levy, et al., "Pilot-Controlled Trial of D-Cycloserine for the Treatment of Post-Traumatic Stress Disorder", International Journal of Neuropsychopharmacology (2002), 5, p. 301-307.
Hofman, "Augmentation of Exposure Therapy with D-Cycloserine for Social Anxiety Disorder", Arch Gen Psychiatry (2006), vol. 63, p. 298-304.
Koch, M., "Investigations in Animal Experiments of Possible Pharmacological Support of Exposition Therapy in Fear and Anxiety Disorders", Nervenarzt, (2002), p. 481-483.
Ledgerwood, "D-Cycloserine and the Facilitation of Extinction of Conditioned Fear: Consequences for Reinstatement", Behavioral Neuroscience, (2003), vol. 118, No. 3, p. 505-513.
Ledgerwood, "D-Cycloserine Facilitates Extinction of Learned Fear: Effects on Reacquisition and Generalized Extinction", Biol. Psychiatry (2005) vol. 57, p. 841-847.
Ledgerwood, "Effects of D-cycloserine on Extinction of Conditioned Freezing", Behavioral Neuroscience, (2003), vol. 117, No. 2, p. 341-349.
Mao, "Extinction of Training in Conjunction with a Partial Agonist of the Glycine Site on the NMDA Receptor Erases Memory Trace", Jour. of Neuroscience (2006), vol. 26(35), p. 8892-8899.
Mothet, "D-Serine is an Endogenous Ligand for the Glycine Site . . . ", Proc. Natl. Acad. Sci. USA., (2000), vol. 97(9), p. 4926-4931.
Nitsche, "Consolidation of Human Motor Cortical Neuroplasticity by D-Cycloserine", Neuropsychopharmacology (2004) vol. 29, p. 1573-1578.
Otto, "Combined Psychotherapy and Pharmacotherapy for Mood and Anxiety Disorders in Adults: Review and Analysis", Clinical Psychology: Science and Practice, (2005), vol. 12(1), p. 72-86.
Papp, M., et al., "Antidepressant-like Effects of 1-aminocyclopropanecarboxylic Acid and D-cycloserine in an Animal Model of Depression", European Journal of Pharmacology 316 (1996) p. 145-151.
Ressler, "Cognitive Enhancers as Adjuncts to Psychotherapy", Archives of General Psychiatry, (2004); vol. 61, p. 1136-1144.
Stickgold, "Sleep-dependent Memory Consolidation", Nature, (2005), vol. 437, p. 1272-1278.
Tsai, "Improved cognition in Alzheimer's Disease with Short-Term D-Cycloserine Treatment", Am J. Psychiatry (1999), vol. 156(3), p. 467-469.
Van Berckel, "Behavioral and Neuroendocrine Effects of the Partial NMDA . . . ", Neuropsychopharmology, (1997), vol. 16(5), p. 317-324.
Wager, "Placebo-Induced Changes in fMRI in the Anticipation and Experience of Pain", Science, (2004), vol. 303, p. 1162-1167.
Walker, "Facilitation of Conditioned Fear Extinction by Systemic Administration or Intra-Amygdala Infusions of D-Cycloserine as Assessed with Fear-Potentiated Startle in Rats", Journal of Neuroscience (2002), vol. 22(6), p. 2343-2351.
Walker, "Practice with Sleep Makes Perfect: Sleep-Dependent Motor Skill Learning", Neuron, (2002), vol. 35, p. 205-211.
Walker, "Sleep-Dependent Learning and Memory Consolidation", Neuron, (2004), vol. 44, p. 121-133.
Yamakura, "Subunit- and Site-Specific Pharmacology of the NMDA Receptor Channel", Progress in Neurobiology, (1999), vol. 59, p. 279-298.

Yates, "The Characterization of Two Novel Series of Glycine Transporter Inhibitors and Potential Utility as Anti-Psychotic Agents", Society for Neuroscience Abstract, (2002), Abstract No. 144.9.

Port, R.L. and Seybold, K.S., "Manipulation of NMDA-Receptor Activity Alters Extinction of an Instrumental Response in Rats", Physiology and Behavior (1998), vol. 64(3), pp. 391-393.

Christoffersen, G.R.J., et al., "Piracetam inhibits Pavlovian extinction and reversal learning in a spatial task for rats", Neuropharmacology (1998), vol. 37, pp. 815-825.

Monti, B., et al., "Subchronic Rolipram Delivery Activates Hippocampal CREB and Arc, Enhances Retention and Slows Down Extinction of Conditioned Fear", Neuropsychopharmacology (2006), vol. 31, pp. 278-286.

Santa Ana, E.J., et al., "D-Cycloserine attenuates reactivity to smoking cues in nicotine dependent smokers: A pilot investigation", Drug and Alcohol Dependence (2009), vol. 104, pp. 220-227.

Anthony, Elizabeth W., et al., "Anxiolytic-like Effects of N-methyl-D-aspartate-associated Glycine Receptor Ligands in the Rat Potentiated Startle Test," European Journal of Pharmacology; 250 (1993) 317-324.

Bouton, Mark E., et al., "State-Department Fear Extinction With Two Benzodiazepine Tranquilizers," Behavioral Neuroscience, 1990, vol. 104, No. 1, 44-55.

Davis, Michael, "Review Article Role of NMDA Receptos and MAP Kinase in the Amygdala in Extinction of Fear: Clinical Implications for Exposure Therapy," European Journal of Neuroscience, vol. 16, pp. 395-398, 2002.

Hofmann, Stefan G., et al., "Augmentation of Exposure Therapy With D-Cycloserine for Social Anxiety Disorder," Arch Gen Psychiatry, vol. 63, pp. 298-304, Mar. 2006.

Ledgerwood, L, et al., "D-Cycloserine Facilitates Extinction of Conditioned Fear as Assessed by Freezing in Rats," Program No. 81.14, 2002, Abstract Viewer/Itinerary Planner, Washington, DC: Society for Neuroscience, 2002. Online.

Otto, Michael W., et al., "Benzodiazepine Use, Cognitive Impairment, and Cognitive-Behavioral Therapy for Anxiety Disorders: Issues in the Treatment of a Patient in Need," J. Clin. Psychiatry 2005; 66 (suppl. 2).

Otto, Michael W., et al., "Clinical Perspectives on the Combination of D-Cycloserine and Cognitive-Behavioral Therapy for the Treatment of Anxiety Disorders," The international Journal of Neuropsychiatric Medicine, CNS Spectr. 2007; 12(a):51-66, 59-69.

Otto, Michael W., et al., "Cognitive-Behavioral Therapy and the Treatment of Panic Disorder: Efficacy and Strategies," J. Clin. Psychiatry 2005; 66 (suppl. 4).

Otto, Michael W., et al., "Combined Psychotherapy and Pharmacotherapy for Mood and Anxiety Disorders in Adults: Review and Analysis," Clinical Psychology: Science and Practice, V12N1, pp. 72-86 (2005).

Parnas, A. Sophie, et al., Effects of Multiple Exposures to D-Cycloserine on Extinction of Conditioned Fear in Rats, Neurobiology of Learning and Memory 83 (2005) 224-231.

Richardson, Rick, et al., "Facilitation of Fear Extinction by D-Cycloserine: Theoretical and Clinical Implications," Learning Memory, 2004, 11: 510-516.

* cited by examiner

A

B

A

B

ACUTE PHARMACOLOGIC AUGMENTATION OF PSYCHOTHERAPY WITH ENHANCERS OF LEARNING OR CONDITIONING

STATEMENT REGARDING FEDERALLY SPONSORED RESEARCH OR DEVELOPMENT

This invention was made with U.S. Government support under grant MH057250 awarded by the National Institutes of Health. The U.S. Government may have certain rights in this invention.

FIELD OF THE INVENTION

The invention relates to methods for treating an individual with a psychiatric disorder with a pharmacologic agent that enhances learning or conditioning in combination with psychotherapy.

BACKGROUND OF THE INVENTION

Classical fear conditioning occurs when an affectively neutral stimulus is paired with a noxious aversive stimulus (unconditioned stimulus [US]) such as footshock. Afterward, the previously neutral stimulus (i.e., now the conditioned stimulus [CS]) is able to elicit a variety of autonomic, hormonal, and skeletal responses that accompany the conscious experience of fear in humans and which are used to operationally define fear in laboratory animals. The fear-eliciting properties of the CS can be extinguished by repeatedly presenting the CS in the absence of the US. It is generally believed that extinction does not reflect unlearning of the original association but involves instead the formation of new associations that compete with the previously conditioned response (see Bouton and Bolles (1985) *Context, Event Memories, and Extinction* (Lawrence Erlbaum Associates, Hillsdale, N.J.); Falls and Davis (1995) "Behavioral and Physiological Analysis of Fear Inhibition," in *Neurobiological and Clinical Consequences of Stress: From Normal Adaptation to PTSD*, eds. Friedman et al. (Lippincott-Raven Publishers, Philadelphia, Pa.); Davis et al. (2000) "Neural Systems Involved in Fear Inhibition: Extinction and Conditioned Inhibition," in *Contemporary Issues in Modeling Psychopathology*, eds. Myslobodsky and Weiner (Kluwer Academic Publishers, Boston, Mass.); Rescorla (2001) "Experimental Extinction," in *Handbook of Contemporary Learning Theories*, eds. Mowrer and Klein (Erlbaurm, Mahwah, N.J.)).

As with fear conditioning itself, fear extinction can be blocked by N-methyl-D-aspartate (NMDA) receptor antagonists administered either systemically (Cox and Westbrook (1994) *Quarterly J. Exp. Psych.* 47B:187-210; Baker and Azorlosa (1996) *Behav. Neuroscience* 110:618-620) or infused directly into the amygdala (Falls et al. (1992) *J. Neuroscience* 12:854-863; 1992; Lee and Kim (1998) *J. Neuroscience* 18:8444-8454). The involvement of the amygdala is of particular interest given the well known involvement of this structure in excitatory fear conditioning (Kapp et al. (1990) "A Neuroanatomical Systems Analysis of Conditioned Bradycardia in the Rabbit," in *Neurocomputation and Learning: Foundations of Adaptive Networks*, eds. Gabriel and Moore (Bradford Books, New York); Fanselow and LeDoux (1999) *Neuron* 23:229-232; Davis (2000) "The Role of the Amygdala in Conditioned and Unconditioned Fear and Anxiety," in *The Amygdala, Volume* 2, ed. Aggleton (Oxford University Press, Oxford, United Kingdom)).

Because NMDA receptor antagonists block extinction, it is possible that NMDA receptor agonists would facilitate extinction. However, the well-documented neurotoxic effects of NMDA receptor agonists argue against their use in humans. For example, increasing attention has focused on partial agonists that might facilitate NMDA receptor activity in a more limited fashion (Lawlor and Davis (1992) *Biological Psychiatry* 31:337-350; Olney (1994) *J. Neural Transmission Suppl.* 43:47-51). In fact, partial agonists such as D-Cycloserine (DCS), a compound that acts at the strychnine-insensitive glycine recognition site of the NMDA receptor complex, have been shown to enhance learning and memory in several animal paradigms including visual recognition tasks in primates (Matsuoka and Aigner (1996) *J. Pharmacol. Exp. Ther.* 278:891-897), eyeblink conditioning in rabbits (Thompson et al. (1992) *Nature* 359:638-641), avoidance learning in rats and mice (Monahan et al. (1989) *Pharmacol., Biochem. Behav.* 34:649-653; Flood et al. (1992) *Eur. J. Pharmacol.* 221:249-254; Land and Riccio (1999) *Neurobiol. Learn. Mem.* 72:158-168), and maze learning in rats and mice (Monahan et al. (1989) *Pharmacol., Biochem. Behav.* 34:649-653; Quartermain et al. (1994) *Eur. J. Pharmacol.* 257:7-12; Pitkanen et al. (1995) *Eur. Neuropsychopharmacol.* 5:457-463; Pussinen et al. (1997) *Neurobiol. Learn. Mem.* 67:69-74), without producing obvious neurotoxicity. DCS has also been found, in some studies, to modestly improve cognition in clinical populations (Javitt et al. (1994) *Am. J. Psychiatry* 151:1234-1236; Schwartz et al. (1996) *Neurology* 46:420-424; Goff et al. (1999) *Arch. General Psychiatry* 56:21-27; Tsai et al. (1999) *Am. J. Psychiatry* 156:467-469), and has been used for many years to treat tuberculosis, again without obvious neurotoxicity.

A reduced ability to extinguish intense fear memories is a significant clinical problem for a wide range of psychiatric disorders including specific phobias, panic disorder, and post-traumatic stress disorder (see Morgan et al. (1995) *Biol. Psychiatry* 38:378-385; Fyer (1998) *Biol. Psychiatry* 44:1295-1304; Gorman et al. (2000) *Am. J. Psychiatry* 157:493-505). Because treatment for these disorders often relies upon the progressive extinction of fear memories (Zarate and Agras (1994) *Psychiatry* 57:133-141; Dadds et al. (1997) *Psychological Bull.* 122:89-103; Foa (2000) *J. Clin. Psychiatry* 61:43-48), pharmacological enhancement of extinction could be of considerable clinical benefit in these conditions.

BRIEF SUMMARY OF THE INVENTION

Methods for treating a psychiatric disorder in an individual are provided. The methods comprise subjecting the individual in need of treatment to at least one session of a combination therapy protocol, where the protocol comprises administering a therapeutically effective amount of a pharmacologic agent that enhances learning or conditioning within about 24 hours prior to conducting a session of psychotherapy. Suitable pharmacologic agents that enhance learning or conditioning include pharmacologic agents that increase the level of norepinephrine in the brain, pharmacologic agents that increase the level of acetylcholine in the brain, and pharmacologic agents that enhance NMDA receptor transmission in the brain. The methods find use in the treatment of a variety of psychiatric disorders, including fear and anxiety disorders, addictive disorders, mood disorders, and movement disorders.

DETAILED DESCRIPTION OF THE INVENTION

Figure 1:
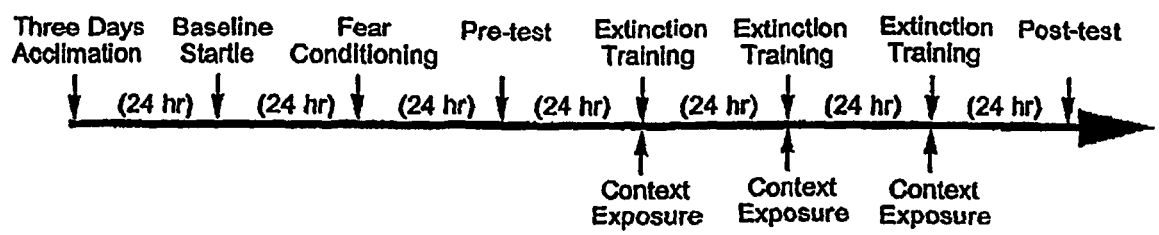
FIG. 1 shows the parametric evaluation of different amounts of extinction training. A. Timeline of the behavioral procedures for Experiment 1. B. Percent fear-potentiated startle measured 24 hrs before (pre-test) and 24 hrs after (post-test) extinction training or context exposure. The control group was tested 2 days after the pre-test, with no intervening exposures. One session of non-reinforced cue exposure produced only modest levels of extinction. Two or three sessions more completely extinguished the fear response. $*p<0.05$ versus context exposure group, $+p<0.05$ versus control group.
Figure 1:
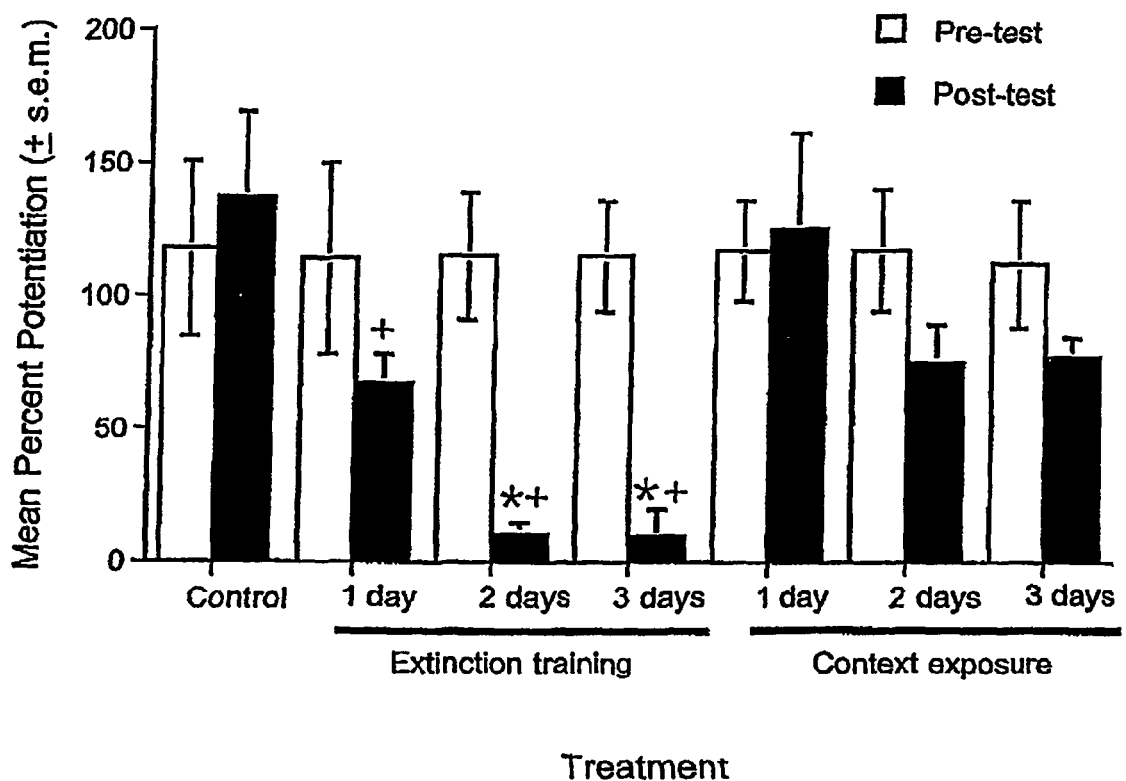

The present invention is directed to methods for treating an individual with a psychiatric disorder. The methods comprise subjecting the individual to one or more sessions of a combination therapy protocol, where the combination therapy protocol comprises an acute administration of a therapeutically effective amount of a pharmacologic agent that enhances learning or conditioning in combination with a session of psychotherapy. By "acute administration" is intended a single exposure of the individual to the therapeutically effective amount of the pharmacologic agent that enhances learning or conditioning, where exposure to the pharmacologic agent occurs within about 24 hours prior to initiating the session of psychotherapy, preferably within about 12 hours, and more preferably within about 6 hours prior to initiating the session of psychotherapy. A full course of treatment for the psychiatric disorder entails at least one session of this combination therapy protocol.

As used herein, "psychiatric disorder" refers to a disorder that can be treated with the methods of the invention. For purposes of the present invention, an individual said to have a psychiatric disorder will have one or more disorders that can be treated with the methods of the invention. Thus an individual may have a single disorder, or may have a constellation of disorders that are to be treated by the methods described herein.

The psychiatric disorders contemplated in the present invention include, but are not limited to, fear and anxiety disorders, addictive disorders including substance-abuse disorders, and mood disorders. Within the fear and anxiety disorder category, the invention encompasses the treatment of panic disorder, specific phobia, post-traumatic stress disorder (PTSD), obsessive-compulsive disorder, and movement disorders such as Tourette's syndrome. The disorders contemplated herein are defined in, for example, the DSM-IV (*Diagnostic and Statistical Manual of Mental Disorders* (4th ed., American Psychiatric Association, Washington D.C., 1994)), which is herein incorporated by reference.

Any pharmacologic agent that is recognized by the skilled artisan as being a pharmacologic agent that enhances learning or conditioning can be used in the methods of the invention. For example, one such class of pharmacologic agents contemplated herein comprises compounds that increase the level of norepinephrine in the brain. Such compounds include those acting as norepinephrine reuptake inhibitors, for example tomoxetine, reboxetine (Edronax or Vestra), duloxetine, venlafaxine (Effexor®), and milnacipran (see, for example, U.S. Pat. No. 6,028,070, the contents of which are herein incorporated by reference), and those compounds that cause release of norepinephrine, for example amphetamine, dextroamphetamine (Dexedrine®), pemoline (Cylert®), and methylphenidate (Ritalin®). Another class of such pharmacologic agents are those compounds that increase the level of acetylcholine in the brain, including, for example, compounds that block its breakdown. Examples of such compounds include, but are not limited to, donepezil HCl or E2020 (Aricept®) and tacrine (THA, Cognex®), which inhibit cholinesterase activity.

Of particular interest are those pharmacologic agents that enhance N-methyl-D-aspartate (NMDA) receptor activation or transmission (cation flow) in the brain without adverse consequences such as neurotoxic effects. Such enhanced NMDA receptor transmission can be measured by a variety of methods known to the skilled artisan. In one embodiment, for example, Luteinizing Hormone (LH) secretion is used as a measure of NMDA receptor activation (see van Berckel et al. (1997) Neuropsychopharm. 16(5):317-324). Other methods include electrophysiological and chemical methods (see Mothet et al. (2000) Proc. Natl. Acad. Sci. USA 97(9):4926-4931). Neurotoxicity can be measured by, for example, the cultured cerebellar granule neuron system described in Boje et al. (1993) Brain Res. 603(2):207-214.

As used herein, the term "NMDA receptor" or 'NMDA channer' refers to the glutamate receptor channel NMDA subtype (Yamakura and Shimoji (1999) Prog. Neurobiol. 59(3):279-298). The term "agonist" encompasses any compound that increases the flow of cations through an ionotrophic receptor such as the NMDA receptor, i.e., a channel opener, and which has not been observed to decrease the flow of cations through the same receptor. "Antagonist" includes any compound that reduces the flow of cations through an ionotropic receptor such as the NMDA receptor, i.e., a channel closer, and which has not been observed to increase the flow of cations through the same receptor. The term "partial agonist" refers to a compound that regulates an allosteric site on an ionotropic receptor, such as the NMDA receptor, to increase or decrease the flux of cations through the ligand-gated channel depending on the presence or absence of the principal site ligand, that is, in the presence or absence of a known endogenous ligand binding to a site on the receptor. In the absence of the principal site ligand, a partial agonist increases the flow of cations through the ligand-gated channel, but at a lower flux than achieved by the principal site ligand. A partial agonist partially opens the receptor channel. In the presence of the principal site ligand, a partial agonist decreases the flow of cations through the ligand-gated channel below the flux normally achieved by the principal site ligand.

As used herein, "NMDA receptor agonist," "NMDA receptor antagonist," and "NMDA receptor partial agonist," may be alternately referred to as "NMDA agonist," "NMDA antagonist," and "NMDA partial antagonist," respectively. Also, "NMDA receptor partial agonist" is intended to be interchangeable with "partial NMDA receptor agonist." The present invention contemplates a variety of molecules acting as such partial NMDA receptor agonists. Examples of such pharmacologic agents include, but are not limited to, compounds that act at the glycine modulatory site of the NMDA receptor (see Yamakura and Shimoji (1999) Prog. Neurobiol. 59(3):279-298), including D-cycloserine (DCS)(see U.S. Pat. Nos. 5,061,721 and 5,260,324), D-serine, and 1-aminocyclopropane-carboxylic acid (ACPC)(see U.S. Pat. Nos. 5,086,072 and 5,428,069, herein incorporated by reference). Other pharmacologic agents that act as partial NMDA agonists, including polyamines such as spermine and spermidine, are also suitable for use in the methods of the present invention (Yamakura and Shimoji (1999) Prog. Neurobiol. 59(3):279-298).

The methods of the invention encompass the use of any type of psychotherapy that is suitable for the particular psychiatric disorder for which the individual is undergoing treatment. Suitable methods of psychotherapy include exposure-based psychotherapy, cognitive psychotherapy, and psychodynamically oriented psychotherapy. See, for example, Foa (2000) J. Clin. Psych. 61(suppl. 5):43-38.

One method of psychotherapy specifically contemplated is the use of virtual reality (VR) exposure therapy to treat a psychiatric disorder using the combination therapy protocol of the invention. VR exposure therapy has been used to treat a variety of disorders including anxiety disorders such as the fear of heights (Rothbaum and Hodges (1999) Behav. Modif. 23(4):507-25), as well as specific phobias, eating disorders, and PTSD (Anderson et al. (2001) Bull. Menninger Clin. 65(1):78-91). Because of the prevalence of PTSD in the general population and the successful use of VR therapy to treat PTSD in, for example, Vietnam veterans (Rothbaum et al. (1999) J. Trauma Stress 12(2):263-71) or rape victims (Rothbaum et al. (2001) J. Trauma Stress 14(2):283-93), one embodiment of the present invention specifically contemplates the use of such VR exposure psychotherapy in combination with a pharmacologic agent as described elsewhere herein to treat PTSD.

The timing of administration and therapeutically effective amount or dose of the particular pharmacologic agent used will depend on the pharmacologic agent itself, with the particular timing and dose selected in order to ensure that a therapeutically effect level of the pharmacologic agent is present in the individual being treated at the time of psychotherapy. In general, the timing of administration will be within about 24 hours before psychotherapy, more preferably within about 12 hours, and still more preferably within about 6 hours. A "therapeutically effective amount" or "therapeutically effective dose" of the pharmacologic agent is that amount of the pharmacologic agent that, when administered in accordance to the combination therapy protocol of the invention, results in an improved therapeutic benefit relative to that observed with psychotherapy in the absence of administering the pharmacologic agent. For example, where the pharmacologic agent is an agent that enhances NMDA receptor activation or transmission in the brain, a therapeutically effective dose or amount is that amount of the pharmacologic agent that enhances NMDA receptor activation or transmission in the brain relative to the level of NMDA receptor activation or transmission in the brain in the absence of administration of the pharmacologic agent. Similarly, when the pharmacologic agent is an agent that increases the level of norepinephrine or acetylcholine in the brain, a therapeutically effective dose or amount is that amount of the pharmacologic agent that increases the level of norepinephrine or acetylcholine in the brain relative to the level of these respective compounds in the brain in the absence of the administration of the pharmacologic agent.

For D-cycloserine, a preferred time of administration is within about 3-8 hours before psychotherapy. For this pharmacologic agent, dosage levels include a low dose level of between about 30-100 mg, and a high dose level of between about 400-500 mg. In one embodiment, D-cycloserine is administered in combination with D-alanine to minimize any potential gastrointestinal effects of this pharmacologic agent.

See U.S. Pat. Nos. 5,061,721 and 5,260,324, herein incorporated by reference.

The therapeutically effective dose of the pharmacologic agent can be administered using any medically acceptable mode of administration. Although the skilled artisan would contemplate any of the modes of administration known to one of ordinary skill, preferably the pharmacologic agent is administered according to the recommended mode of administration, for example, the mode of administration listed on the package insert of a commercially available agent.

A subject undergoing treatment with the methods of the invention exhibits an improvement in one or more symptoms associated with the psychiatric disorder. For a description of the relevant symptoms, see, for example, the DSM-IV ((1994) *Diagnostic and Statistical Manual of Mental Disorders* (4th ed., American Psychiatric Association, Washington D.C.)), which is herein incorporated by reference. The efficacy of the methods of the invention can be assessed using any clinically recognized assessment method for measuring a reduction of one or more symptoms of the particular psychiatric disorder. Examples of such assessment methods are described in, for example, Experiment 7, provided below.

The present invention may be better understood with reference to the following examples. These examples are intended to be representative of specific embodiments of the invention, and are not intended as limiting the scope of the invention.

EXPERIMENTAL

Experiments 1-6 were conducted to examine the effects of the partial NMDA receptor agonist D-cycloserine on conditioned fear extinction. These experiments were conducted using Adult male Sprague-Dawley rats as described in the Materials and Methods section below. Experiment 7 describes a clinical trial of D-cycloserine augmentation of behavioral exposure therapy for human subjects suffering from a specific phobia.

Materials and Methods for Experiments 1-6

Animals

Adult male Sprague-Dawley rats (Charles River, Raleigh, N.C.) weighing between 300 and 400 g were used. Animals were housed in group cages of four rats each in a temperature (24° C.) controlled animal colony, with continuous access to food and water. They were maintained on a 12:12 light-dark cycle with lights on at 0700 hrs. All behavioral procedures took place during the rats' light cycle. A total of 178 rats were used.

Apparatus

Animals were trained and tested in 8×15×15-cm Plexiglas and wire mesh cages. The cage floor consisted of four 6.0-mm diameter stainless steel bars spaced 18 mm apart. Each cage was suspended between compression springs within a steel frame and located within a custom-designed 90×70×70-cm ventilated sound-attenuating chamber. Background noise (60 dB wide-band) was provided by a General Radio Type 1390-B noise generator (Concord, Mass.) and delivered through high frequency speakers (Radio Shack Supertweeter; Tandy, Fort Worth, Tex.) located 5 cm from the front of each cage. Sound level measurements (SPL) were made with a Bruel & Kjaer (Marlborough, Mass.) model 2235 sound-level meter (A scale; random input) with the microphone (Type 4176) located 7 cm from the center of the speaker (approximating the distance of the rat's ear from the speaker).

Startle responses were evoked by 50-ms 95-dB white-noise bursts (5 ms rise-decay) generated by a Macintosh G3 computer soundfile (0-22 kHz), amplified by a Radio Shack amplifier (100 Watt; Model MPA-200; Tandy, Fort Worth, Tex.), and delivered through the same speakers used to provide background noise. An accelerometer (model U321AO2; PCB Piezotronics, Depew, N.Y.) affixed to the bottom of each cage produced a voltage output proportional to the velocity of cage movement. This output was amplified (PCB Piezotronics, Model 483B21) and digitized on a scale of 0-2500 units by an InstuNET device (GW Instruments, Model 100B; Somerville, Mass.) interfaced to a Macintosh G3 computer. Startle amplitude was defined as the maximal peak-to-peak voltage that occurred during the first 200 ms after onset of the startle-eliciting stimulus.

The CS was a 3.7-s light (82 lux) produced by an 8-W fluorescent bulb (100-µs rise time) located 10 cm behind each cage. Luminosity was measured using a VWR light meter (Atlanta, Ga.). The unconditioned stimulus was a 0.5-s shock, delivered to the floorbars, and produced by a LeHigh Valley shock generator (SGS-004; LeHigh Valley, Beltsville, Md.). Shock intensities (measured as in Cassella et al. (1986) *Physiol. Behav.* 36:1187-1191) were 0.4 mA. The presentation and sequencing of all stimuli were under the control of the Macintosh G3 computer using custom-designed software (The Experimenter, Glassbeads Inc.; Newton, Conn.).

Surgery and Histology

Rats that were to receive intra-amygdala infusions (Experiment 6) were anesthetized with Nembutal (sodium pentobarbital, 50 mg/kg, i.p) and placed in a stereotaxic frame (ASI Instruments, Inc., Warren, Mich. The skull was exposed and 22-gauge guide cannulae (model C313G, Plastics One, Inc.; Roanoke, Va.) were implanted bilaterally into the basolateral nucleus of the amygdala (AP=−2.8; DV=−9.0; ML=±5.0 from bregma). Dummy Cannulae (model C313DC, Plastics One, Inc.) were inserted into each cannula to prevent clogging. These extended approximately 1 mm past the end of the guide cannula. Screws were anchored to the skull and the assembly was cemented in place using dental cement (The Hygenic Corp., Akron, Ohio).

Behavioral procedures began either 10 or 11 days after surgery. Cannulated rats subsequently received a chloral hydrate overdose and were perfused intracardially with 0.9% saline followed by 10% formalin. The brains were removed and immersed in a 30% sucrose-formalin solution for at least 3 d, after which 40-µm coronal sections were cut through the area of interest. Every fourth section was mounted and stained with cresyl violet.

Drug Administration

Systemic administration: D-Cycloserine (Sigma-Aldrich, St. Louis, Mo.)—(3.25, 15, and 30 mg/kg)—and (±)-HA-966 (Research Biochemicals, Inc., Natick, Mass.)—(6 mg/kg) were freshly dissolved in saline and injected intraperitoneally 30 min prior to extinction training. Drug doses were chosen based on preliminary findings (data not shown), on the results of other behavioral studies (e.g., Monahan et al. (1989) *Pharmacol. Biochem. Behav.* 34:649-653; Flood et al. (1992) *Eur. J. Pharmacol.* 221:249-254; Moraes Ferreira and Morato (1997) *Alcohol Clin. Exp. Res.* 21:1638-1642; Pussinen et al. (1997) *Neurobiol. Learn. and Mem.* 67:69-74; Land and Riccio (1999) *Neurobiol. Learn. Mem.* 72:158-168), on estimates of brain concentration following systemic administration (extrapolated from Loscher et al. (1994) *Brit. J. Pharmacol.* 112:97-106) together with findings relating drug concentrations in vitro to DCS effects on NMDA receptor function measured electrophysiologically (e.g., Watson et al. (1990)

Brain Res. 510:158-160; Priestley and Kemp (1994) *Molecular Pharmacol.* 46:1191-1196) or vis-à-vis ligand binding to the use-dependent channel-associated binding site (Hood et al. (1989) *Neuroscience Letters* 98:91-95; Hamelin and Lehmann (1995) *Eur. J. Pharmacol.* 281:R11-13), and on the ability of systemically administered DCS to influence NMDA receptor-mediated cGMP concentrations in mouse cerebellum (Emmett et al. (1991) *Neuropharmacol.* 30:1167-1171).

Intra-Amygdala Infusion: DCS (10 µg/side) or saline was infused (0.25 µl/min) through 28-gauge injection cannulas (model C313I, Plastic Products) 20 min prior to extinction training. The total volume infused was 0.5 µl/side. The infusion cannulae were left in place for 2 minutes before being withdrawn.

General Behavioral Procedures

Behavioral procedures for all experiments consisted of an acclimation phase, a baseline startle test, a fear conditioning phase, a pre-extinction test, extinction training, and a post-extinction test (see FIG. 1A).

Acclimation. On each of three consecutive days, rats were placed into the test chambers for 10 min and then returned to their home cages.

Baseline startle test. On each of the next two consecutive days, animals were placed in the test chambers and presented with 30 95-dB noise bursts at a 30-s interstimulus interval (ISI). Animals whose baseline startle was less than 1% of the possible accelerometer output were excluded insofar as fear-potentiated startle cannot be properly measured with such a low baseline (a total of 2 rats out of 144 were excluded on this basis).

Fear conditioning. 24 hrs later, rats were returned to the test chambers and 5 minutes later given the first of 10 light-footshock pairings. The 0.4-mA 0.5-s shock was delivered during the last 0.5 sec of the 3.7-sec light. The average inter-trial interval was 4 min (range=3-5 min).

Pre-extinction test. 24 hrs after fear conditioning, rats were returned to the test chambers and 5 min later were presented with 30 95-dB noise bursts (30-s ISI). These initial startle stimuli were used to habituate the startle response to a stable baseline prior to the noise alone and light-noise test trials that followed. A stable baseline, in turn, reduces variability in the fear-potentiated startle measure described below. Thirty seconds later, 20 additional noise bursts were presented (ISI=30 s). Half of these were presented in darkness (noise alone test trial) and half were presented 3.2 s after onset of the 3.7-s light (light-noise test trial). The order of these two trial types was randomized with the constraint that no two trial types occurred more than twice in a row. Percent fear-potentiated startle was computed as [(startle amplitude on light-noise minus noise-alone trials)/noise-alone trials]×100. Based on these data, rats were sorted into equal size groups such that each group had comparable mean levels of percent fear-potentiated startle. Because the fear-potentiated startle test is itself an extinction procedure (i.e., CS presentations without shock), and because we wanted to minimize any incidental extinction prior to explicit extinction training with drug, a minimal number of CS presentations was used in this test compared to the more lengthy post-extinction test described below. We have found, however, that this abbreviated test is adequate for matching rats into different groups with comparable levels of fear-potentiated startle.

Extinction training. 24 hrs after the pre-extinction test, rats were returned to the test chamber and 5 min later received 30 3.7-s light exposures without shock (ISI=30 s). Control rats were placed in the test cages and remained there for the same amount of time as rats in the extinction groups, but did not receive non-reinforced CS presentations. Rats in Experiment 1 received either 1, 2, or 3 sessions of extinction training with a 24-hr interval between each. Rats in all other experiments received a single session of extinction training.

Post-extinction test. 24 hrs after the last extinction session, rats were returned to the test chamber and, 5 min later, were presented with 30 95-dB noise bursts, as in the pre-extinction short-test, to habituate the startle response to a stable baseline prior to the noise alone and light-noise test trials that followed. 30 s later, 60 inter-mixed noise alone and light-noise test trials (95 dB, ISI=30 s) were presented. Percent potentiated startle was calculated from the noise alone and light-noise test trials as previously described.

Statistics

ANOVA on percent fear-potentiated startle scores was the primary statistical measure. Between group comparisons were also made using two-tailed t-tests for independent samples. The criterion for significance for all comparisons was $p<0.05$.

Results

Experiments 1-6

Experiment 1

Parametric Evaluation of Different Amounts of Extinction Training

This experiment assessed the effect on fear-potentiated startle of 1, 2, or 3 days of extinction training. 42 rats were matched into 7 groups of 6 animals each based on their level of fear-potentiated startle in the pre-extinction test. Beginning 24 hrs after the pre-extinction test, rats received 1, 2, or 3 consecutive days of extinction training (30 non-reinforced light presentations per day), or 1, 2, or 3 days of exposure to the context without extinction training. An additional control group was tested 2 days after the pre-extinction test without intervening exposures to either context or the visual CS.

FIG. 1B shows that after 1 day of extinction training, fear-potentiated startle was reduced by approximately 35% compared to the pre-extinction test. After 2 or 3 days, fear-potentiated startle was reduced by approximately 90%. A two-way ANOVA with Treatment (non-reinforced CS presentations versus context exposure alone) and Days (one, two, or three extinction sessions) as between-subjects factors indicated a significant Treatment effect, $F(1, 30)=13.01$, and also a significant Treatment X Days interaction, $F(2, 30)=8.90$. Thus, the reduction of fear-potentiated startle across days was greater in the groups that received non-reinforced CS exposures than in the groups that received context exposure alone. Individual comparisons between non-reinforced CS presentation and context-exposure groups indicated significant differences after 2, $t(10)=3.41$, and after 3, $t(10)=6.37$, days. Significant differences versus the non-exposed control group were found versus rats that received one, $t(10)=2.30$, two, $t(10)=4.33$, or three, $t(10)=4.26$, days of extinction training.

Experiment 2

Dose-Response Function for the Effect of DCS on Extinction

Twenty-seven rats were acclimated, tested for baseline startle, fear-conditioned, and tested for fear-potentiated startle as previously described. Rats were then divided into 4 groups of 7 animals each (except the DCS 30 mg/kg where N=6] based on their pre-extinction level of fear-potentiated startle. 24 hrs later, each rat was injected with either saline or DCS (3.25, 15, or 30 mg/kg; i.p.). Thirty min later, rats received a single session of extinction training. A single extinction session was used because the results of Experiment 1 indicated that this produced a minimal amount of extinction against which a facilitatory effect of DCS could be detected. Twenty-four hours later, rats were tested for fear-potentiated startle without drug injections in order to evaluate the effect on extinction of the previous drug treatments.

Figure 2:
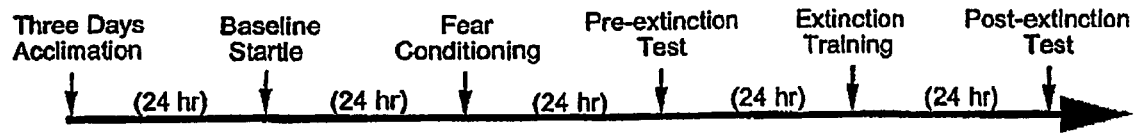
FIG. 2 shows the dose-response function for the effect of DCS on extinction. A. Timeline of the behavioral procedures for Experiment 2. B. Percent fear-potentiated startle measured 24 hrs before and 24 hrs after a single session of extinction training in rats injected with saline or DCS (3.25, 15, or 30 mg/kg, i.p.) 30 min prior to non-reinforced cue exposure. DCS dose-dependently facilitated extinction learning. $*p<0.05$ versus saline post-extinction.
Figure 2:
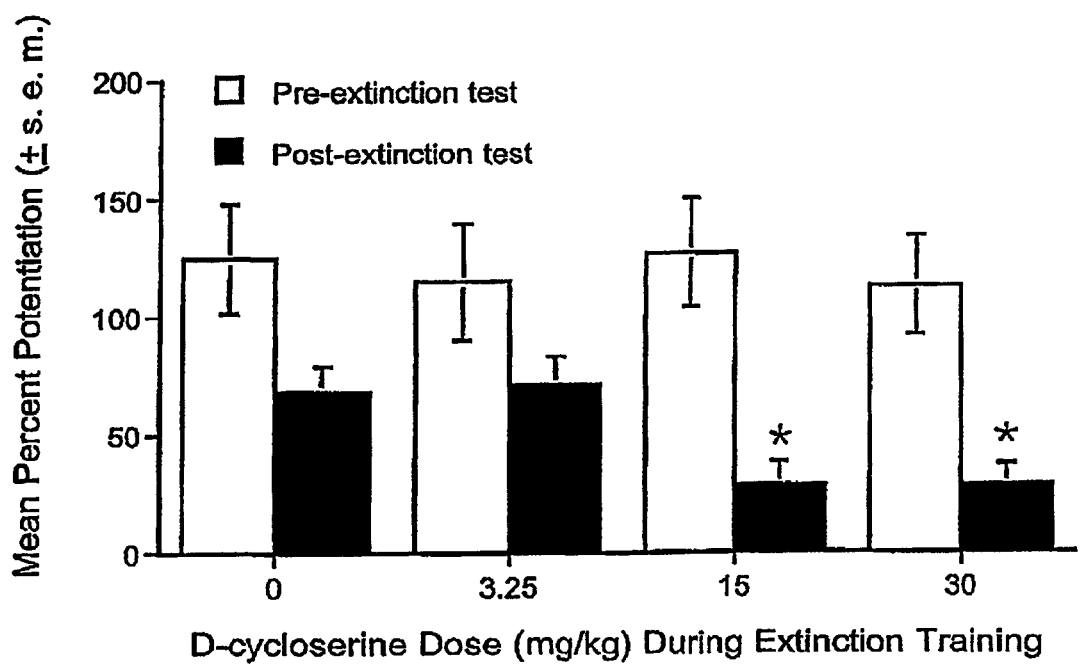

DCS facilitated extinction in a dose-dependent manner (FIG. 2B). ANOVA indicated a significant Dose effect, $F(3, 23)=3.02$, with a significant linear trend, $F(1,23)=7.26$. Fear-potentiated startle was significantly lower in rats injected with 15 and 30 mg/kg DCS prior to extinction training, $t(12)=2.61$ and $t(11)=2.53$, for 15 and 30 mg/kg versus saline, respectively. Because 15 mg/kg produced the maximal enhancing effect, we used this dose in our subsequent experiments.

Experiment 3

Effect of DCS in Non-Extinguished Rats

To test whether the effects of DCS reflected an augmentation of extinction per se, or reflected, instead, a disruption of fear-potentiated startle independent of extinction (e.g., a delayed effect on the expression of fear-potentiated startle 24 hours after drug administration), additional rats were tested with and without extinction training. For this experiment, 28 rats were matched into 4 groups of 7 animals each based on the pre-test. 24 hrs later, each rat was injected with either saline or DCS (15 mg/kg) and returned to its home cage until placed in the startle chamber 30 min later. Two groups (one group of saline-injected rats and one group of DCS-injected rats) underwent extinction training. Two other groups (one group of saline-injected rats and one group of DCS-injected rats) were placed into the test chamber but did not receive extinction training. 24 hrs later, all groups were tested for fear-potentiated startle without drug injections.

Figure 3:
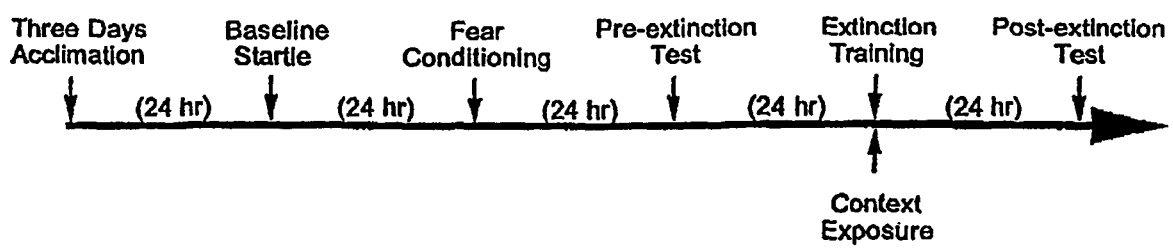
FIG. 3 shows the effect of DCS in non-extinguished rats. A. Timeline of the behavioral procedures for Experiment 3. B. Percent fear-potentiated startle measured 24 hrs before and 24 hrs after extinction training. Saline or DCS (15 mg/kg, i.p.) was administered 30 min prior to a single session of either extinction training (cue exposure) or context alone exposure. Fear-potentiated startle was significantly lower in rats that received DCS+extinction training than in rats that received saline+extinction training. Fear-potentiated startle was not appreciably affected by DCS in rats that did not receive extinction training. $*p<0.05$ versus saline+extinction training.
Figure 3:

FIG. 3B shows that fear-potentiated startle in rats receiving DCS plus extinction training was significantly lower than in rats that received saline plus extinction training, $t(12)=3.02$. This replicates the principal finding of Experiment 2. The novel finding here is that fear-potentiated startle in rats that received DCS without extinction training was comparable to fear-potentiated startle in rats that received saline without extinction training. Thus, the effect of DCS noted in Experiment 2, and replicated here, appears to reflect a specific influence on extinction and not a more general effect on fear-potentiated startle measured 24 hours later in the absence of the drug.

Experiment 4

Effect of the Strychnine-Insensitive Glycine Recognition Site Antagonist, HA-966, on Extinction and on the Facilitation of Extinction by DCS If DCS facilitates extinction by acting as an agonist at the strychnine-insensitive glycine recognition site, then the effect of DCS should be blocked by a strychnine-insensitive glycine site antagonist. To test this, 28 rats were matched into 4 groups of 7 animals each based on the pre-extinction test. 24 hrs later, each rat was injected with either saline or HA-966 (6 mg/kg) followed 10 min later by a second injection of either saline or DCS (15 mg/kg). This dose was chosen based on pilot experiments suggesting that higher doses of HA-966 alone blocked extinction, thereby complicating interpretations of interactive DCS/HA-966 effects. 30 min later, rats received a single session of extinction training and, 24 hrs later, were tested for fear-potentiated startle with no drug injections.

Figure 4:
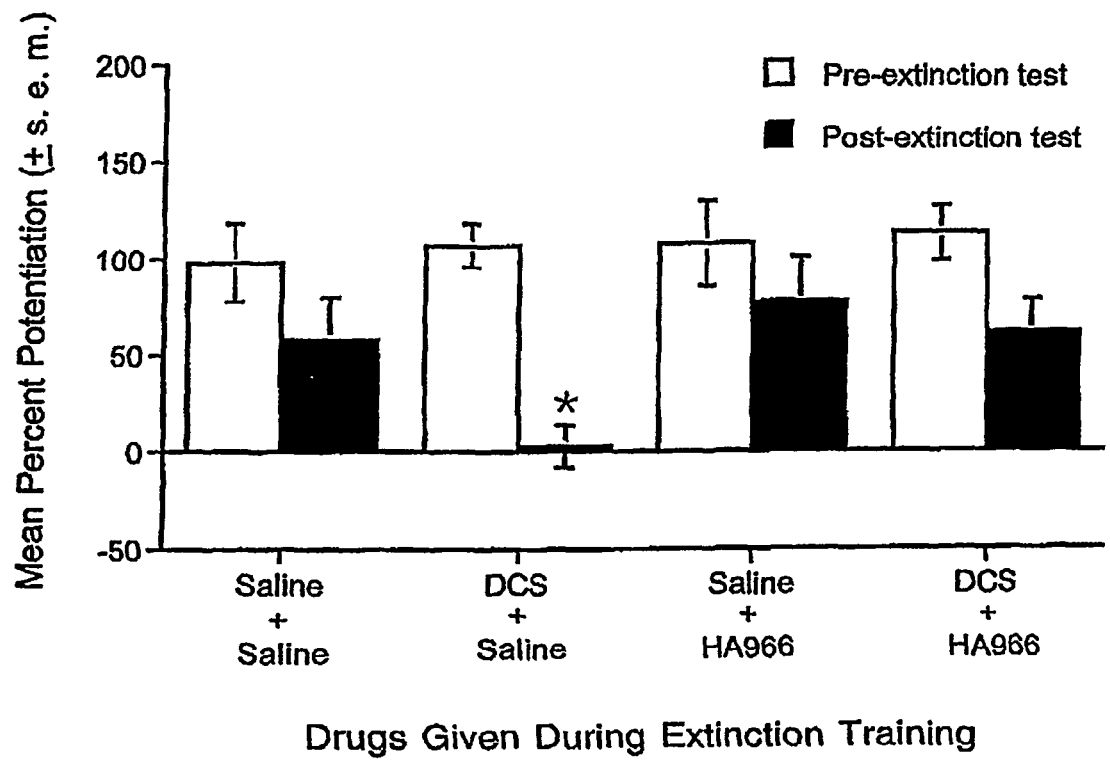
FIG. 4 shows the effect of the strychnine-insensitive glycine recognition site antagonist HA-966 on extinction and on the facilitation of extinction by DCS. A. Timeline of the behavioral procedures for Experiment 4. B. Percent fear-potentiated startle measured 24 hrs before (pre-extinction test) and 24 hrs after (post-extinction test) extinction training. Saline or HA-966 (6 mg/kg, i.p.) were administered 10 min before a second injection of saline or DCS, followed 30 min later by a single session of extinction training. HA-966 completely blocked the effects of DCS but did not, on its own, noticeably influence extinction at this dose. $*p<0.05$ versus all other groups.

HA-966 completely blocked the enhancement of extinction produced by DCS, but did not itself influence extinction when administered alone (FIG. 4B). Replicating findings from experiments 2 and 3, fear-potentiated startle was significantly lower in rats injected with saline+DCS compared to rats injected with saline+saline, $t(12)=2.73$. This effect was blocked by HA-966. Fear-potentiated startle in rats injected with HA-966+DCS was not significantly different from fear-potentiated startle in rats injected with saline+saline, but was significantly different from fear-potentiated startle in rats injected with saline+DCS, $t(12)=3.35$. Overall, these results suggest that the facilitatory effect of DCS on extinction is most likely mediated by the NMDA receptor.

Experiment 5

Effect of Pre-Test DCS and HA-966 Administration on Fear-Potentiated Startle

This experiment evaluated whether the effect of DCS or HA-966 might be secondary to effects on fear itself or on CS processing. For example, if DCS increases CS-elicited fear, this might facilitate extinction by increasing the discrepancy between what the CS predicts and what actually occurs (Wagner and Rescorla (1972) "inhibition in Pavlovian Conditioning: Application of a Theory," in *Inhibition and Learn.*, eds. Boakes and Halliday (Academic Press, London)). If HA-966 interferes with visual processing, this might block extinction produced by non-reinforced exposures to the visual CS. To evaluate these possibilities, 17 rats (Saline, N=5; DCS, N=6; HA-966, N-6) were acclimated, tested for baseline startle, and fear-conditioned as previously described. 24 hrs later, rats were injected with saline, DCS (15 mg/kg), or HA-966 (6 mg/kg). 30 (for DCS) or 40 (for HA-966) minutes after the injections, rats were tested for fear-potentiated startle.

Figure 5:
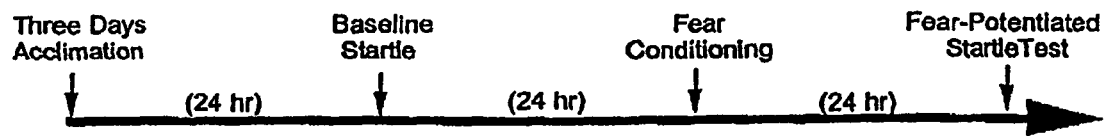
FIG. 5 shows the effect of pre-test DCS and HA-966 administration on fear-potentiated startle. A. Timeline of the behavioral procedures for Experiment 5. B. Percent fear-potentiated startle measured 24 hrs after fear-conditioning in rats receiving pre-test injections of saline, DCS (15 mg/kg), or HA-966 (6 mg/kg). Neither drug had any discernible effect on fear-potentiated startle.
Figure 5:
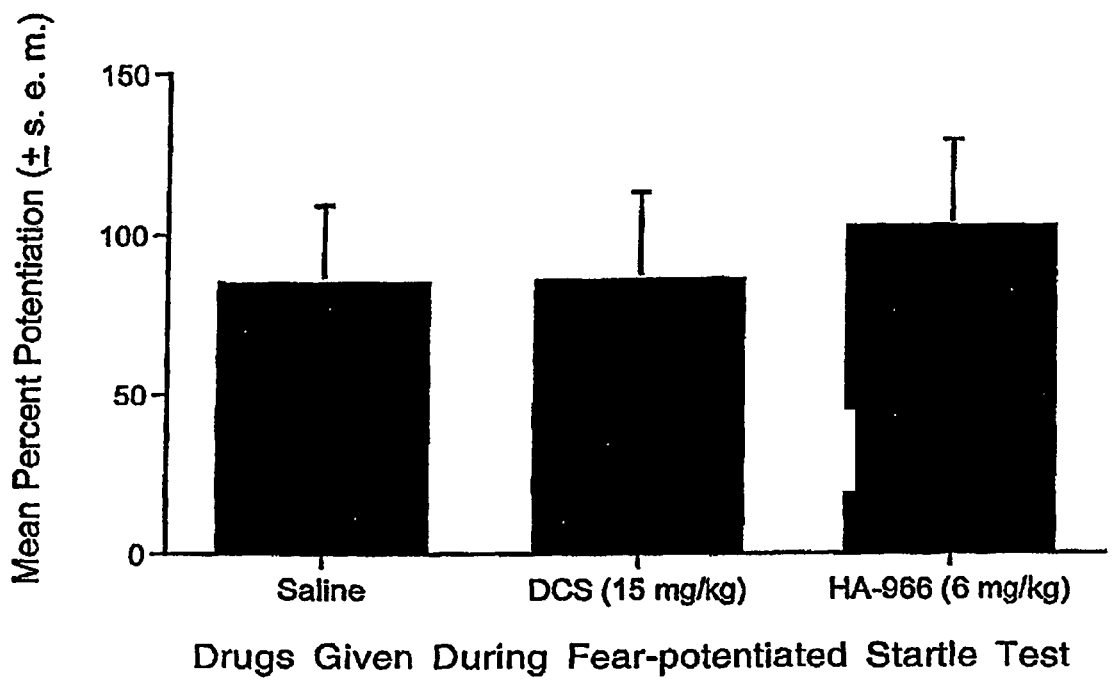

As shown in FIG. 5B, neither DCS nor HA-966 significantly influenced fear-potentiated startle when injected prior to testing. Thus, it is unlikely that these compounds influence extinction by increasing fear or by disrupting CS processing. In fact, a previous study reported a modest anxiolytic effect of both compounds on fear-potentiated startle (Anthony and Nevins (1993) *Eur. J. Pharmacol.* 250:317-324), although at doses higher than those used in the present study. Anxiolytic effects of DCS have also been reported with the elevated plus-maze (Karcz-Kubicha et al. (1997) *Neuropharmacol.* 36:1355-1367) and, at very high doses, with the Vogel-conflict procedure (Klodzinska and Chojnacka-Wojcik (2000) *Psychopharmacologia* 152:224-228).

Experiment 6

Effect of Intra-Amygdala DCS Infusions on Extinction

Previous studies indicate that NMDA receptors in the amygdala play a critical role in the extinction of conditioned fear (Falls et al. (1992) *J. Neuroscience* 12:854-863; Lee and Kim (1998) *J. Neuroscience* 18:8444-8454). It is possible that the effect of systemically administered DCS reported in the above experiments was mediated by actions at amygdala NMDA receptors. To determine if the effect of systemically administered DCS would be mimicked by intra-amygdala DCS infusions, 36 rats with intra-amygdala cannulations received fear conditioning, extinction training, and testing for fear-potentiated startle as previously described. 15 minutes before being placed into the test chamber for extinction training, rats were infused with either phosphate-buffered saline (PBS) or DCS (10 μg/side) (preliminary findings suggested a weak effect of 1 μg/side and a more potent effect of 10 μg/side). One group of PBS-infused rats and one group of DCS-infused rats received extinction training. An additional group of PBS- and an additional group of DCS-infused rats were not placed in the test chamber and did not receive extinction training. Note that this procedure differed from that of Experiment 3 in which control rats received context exposure. Because context exposure constitutes context extinction, and because we were particularly concerned in this experiment that intra-amygdala DCS infusions might be associated with neurotoxicity, we wanted to ensure that any loss of fear-potentiated startle following intra-amygdala infusions could unambiguously be attributed to amygdala damage. If, for example, control rats that had received context extinction showed a reduction of CS-elicited fear, it would be unclear if this was attributable to a DCS-induced lesion or due, instead, to an unintended effect of context extinction on fear to the visual CS. Rats in all groups were tested 24 hours later without drug infusions.

Figure 6:
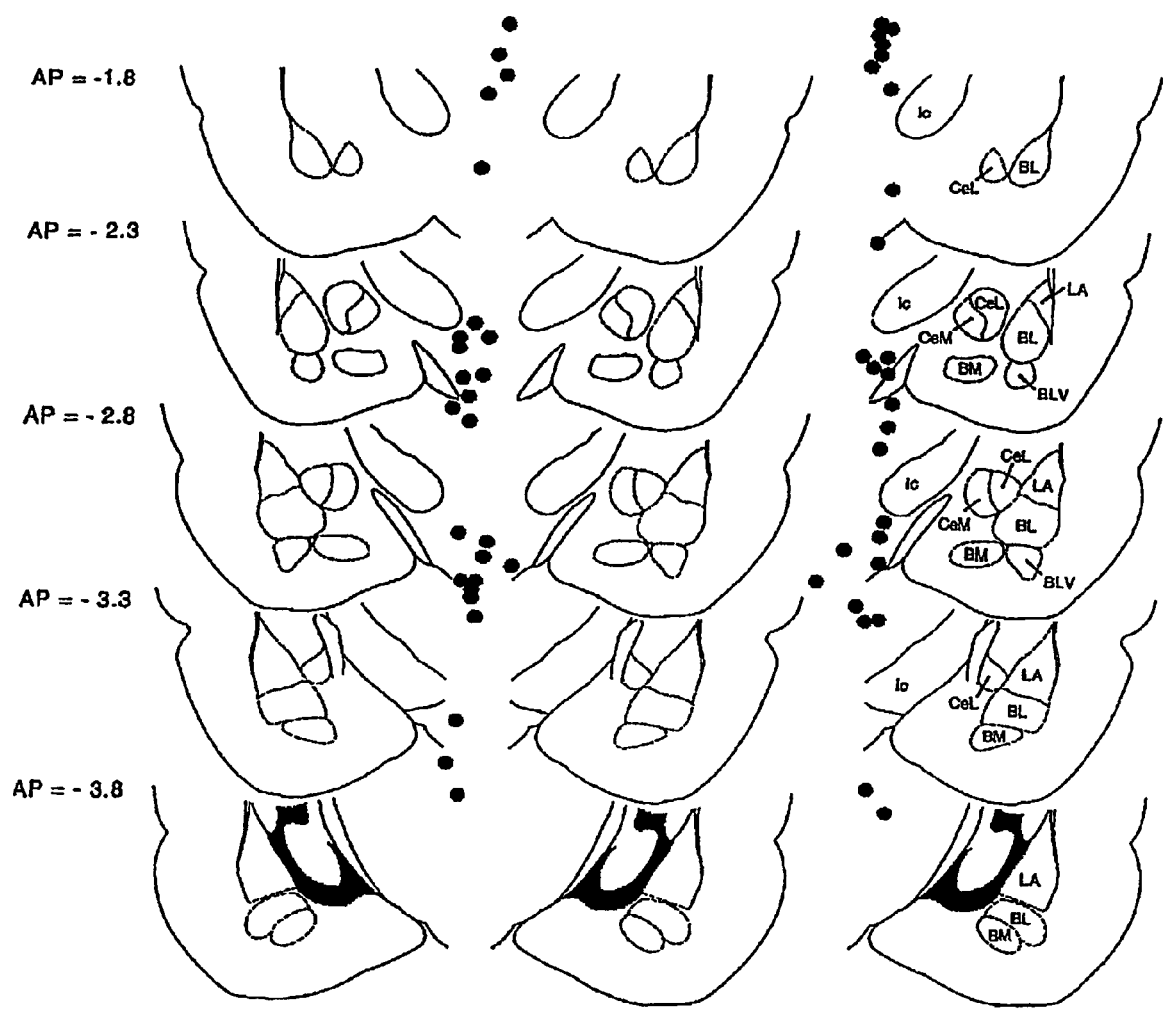
FIG. 6 shows cannula tip placements transcribed onto atlas plates adapted from Paxinos and Watson ((1997) *The Rat Brain in Stereotaxic Coordinates* ($3^{rd}$ ed., Academic Press, New York)). The distance from bregma is indicated to the left; nuclei within the plane of section are identified to the right. BM=basomedial amygdaloid nucleus; BL=basolateral amygdaloid nucleus; BLV=basolateral amygdaloid nucleus, ventral part; CeM=central amygdaloid nucleus, medial division; CeL=central amygdaloid nucleus, lateral division; ic=internal capsule; LA=lateral amygdaloid nucleus; OPT=optic tract.
Figure 7:
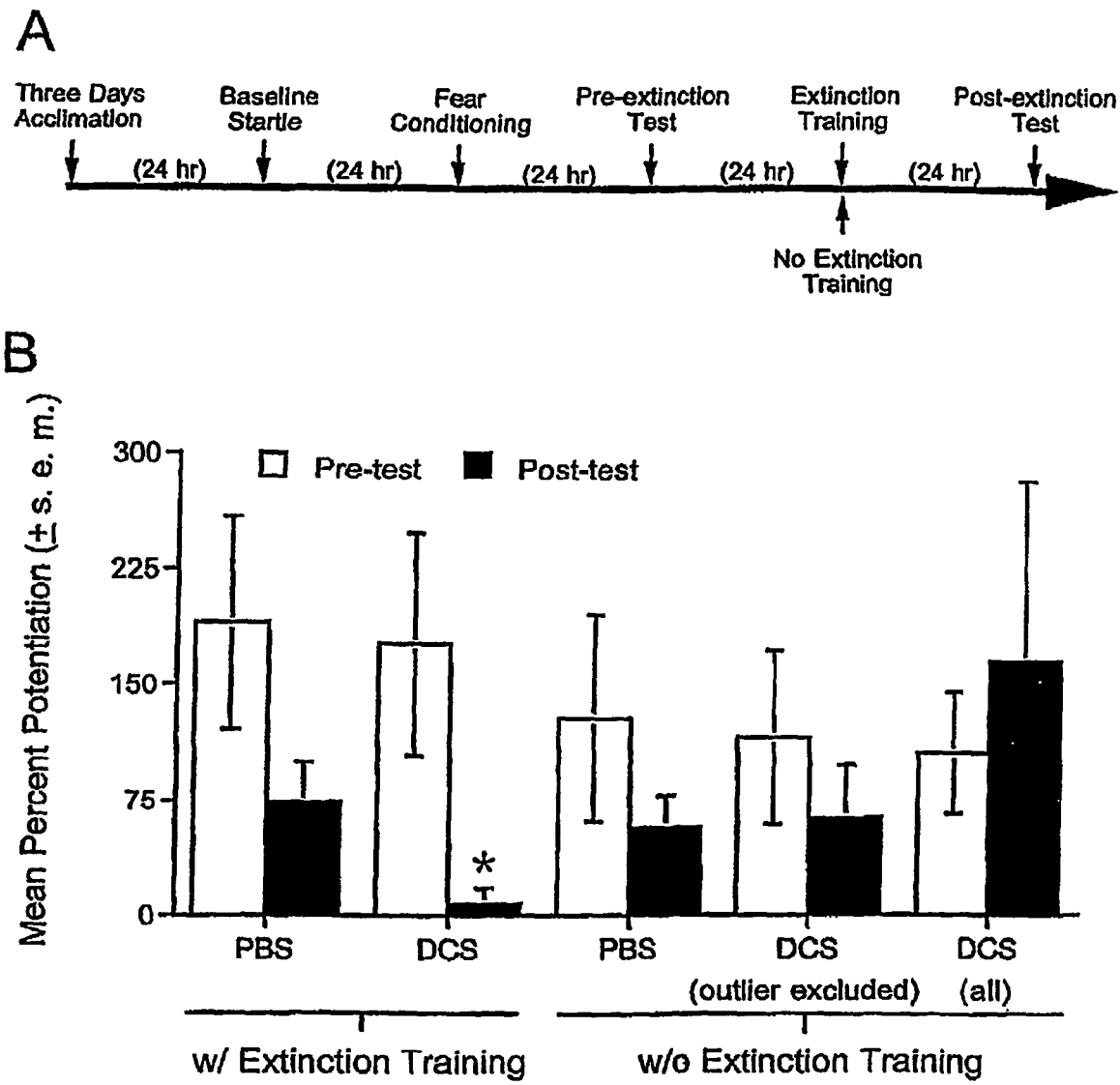
FIG. 7 shows the effect of intra-amygdala DCS infusions. A. Timeline of the behavioral procedures for Experiment 3. B. PBS or D-Cycloserine (10 µg/side) was infused into the amygdala 15 min prior to extinction training. Other rats received DCS without extinction training. When tested 24 hrs later, fear-potentiated startle was significantly lower in rats that received DCS+extinction training than in rats that received PBS+extinction training. Fear-potentiated startle was not appreciably affected by DCS in rats that did not receive extinction training. For the group that received DCS without extinction training, mean percent potentiation was calculated with and without data from a single outlier who had an a typically high percent potentiation score. $*p<0.05$ versus all other groups.

Behavioral data for 10 rats were excluded because the placements for these rats were located outside of the amygdala, resulting in group N's of 9 (PBS—extinction), 9 (DCS—extinction), 4 (PBS—no extinction), and 4 (DCS—no extinction). Placements for the remaining rats are shown in FIG. 6, and the behavioral results are shown in FIG. 7. ANOVA indicated a significant Treatment (DCS versus PBS) X Training (extinction versus no extinction) interaction, $F(1, 22)=5.05$. Fear-potentiated startle was significantly lower in rats that received intra-amygdala DCS infusions prior to extinction training compared to rats that received intra-amygdala PBS infusions prior to extinction training, $t(16)=2.49$, and was also significantly lower than in rats that received DCS without extinction training, $t(11)=2.36$. Fear-potentiated startle was not significantly different in rats that received PBS versus DCS infusions and no extinction training. The latter result suggests that the effect of DCS in rats that received extinction training is not attributable to neurotoxic DCS effects insofar as this would have disrupted fear-potentiated startle in both groups. In fact, fear-potentiated startle was unusually high in non-extinguished rats that received DCS infusions. This was largely attributable to a single rat with a percent increase score of 465%. Even with this outlier excluded, fear-potentiated startle was not significantly different in rats that received PBS versus DCS infusions and no extinction training. As before, however, fear-potentiated startled was significantly lower in rats that received intra-amygdala DCS infusions prior to extinction training compared to rats that received intra-amygdala DCS infusions without extinction training, $t(10)=2.34$.

Figure 8:
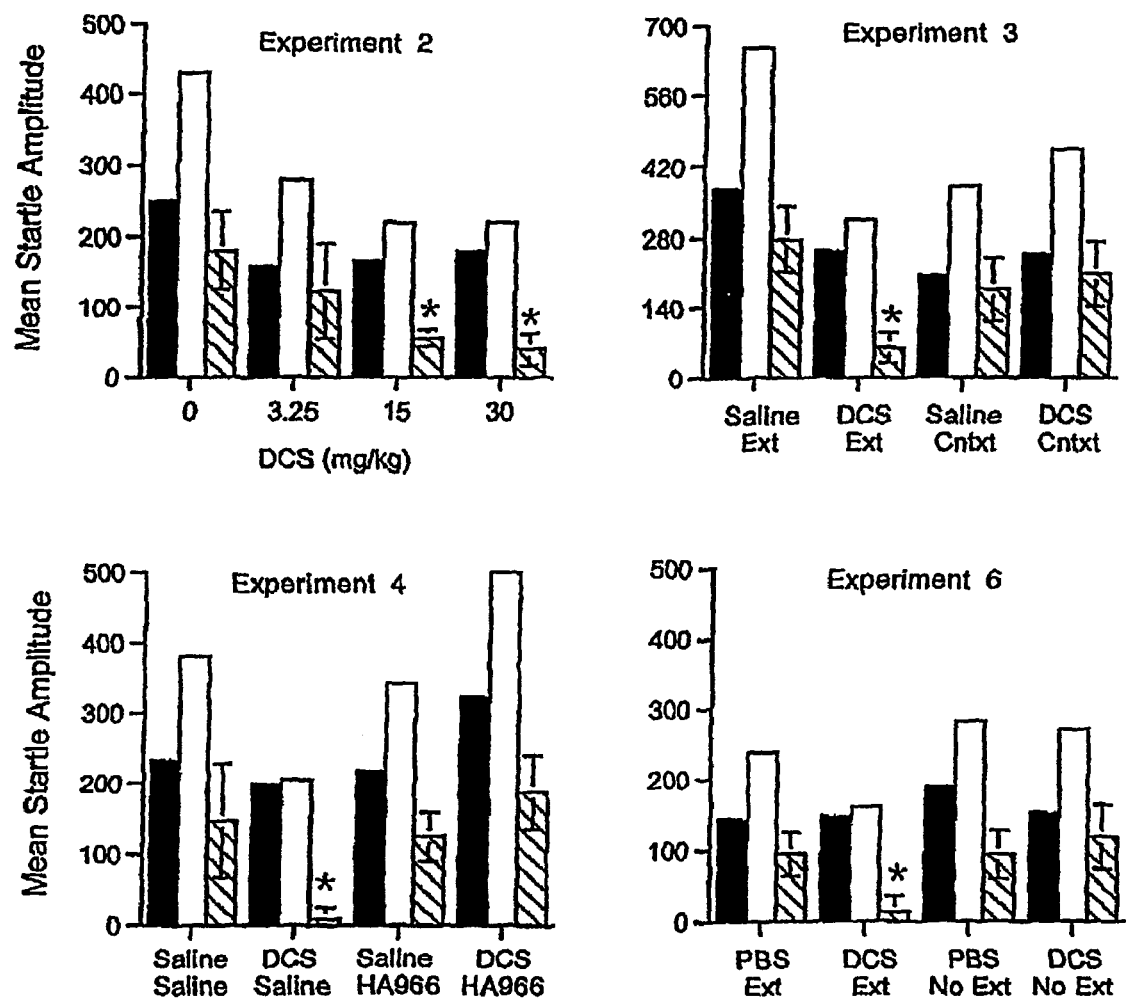
FIG. 8 is a composite figure showing absolute startle values for all rats receiving drugs prior to extinction training. Dark bars indicate baseline startle amplitude on noise alone trials; open bars indicate startle amplitude on light-noise trials. The difference between these two (i.e., fear-potentiated startle) is indicated by the striped bars. In no case were significant differences found in baseline startle during the fear-potentiated startle test 24 hrs after drug administration. Moreover the statistical results were similar when absolute difference scores (i.e., startle amplitude on light-noise trials minus startle amplitude on noise alone trials) rather than percent potentiation scores were analyzed. $*p<0.05$ (except Panel C, p=0.087) versus all left-most bars.

Effects of DCS and HA-966 on Extinction Are Not Due to Changes in Baseline Startle FIG. 8 shows absolute startle values from Experiments 2, 3, 4, and 6 (all experiments showing drug effects on extinction). Significant drug effects on baseline startle were not found in any experiment when measured in the extinction test 24 hours later. Moreover, the statistical results from analyses of percent potentiation scores were mostly comparable to results obtained using absolute difference scores. Thus, DCS dose-dependently facilitated extinction, $F(1,24)=6.03$ (experiment 2). Fear-potentiated startle in the DCS+extinction group was significantly different from fear-potentiated startle in the saline+extinction group in Experiment 3, $t(12)=3.21$, and fear-potentiated startle was comparable in saline and DCS groups that did not receive extinction training. The difference between fear-potentiated startle in DCS+saline injected versus DCS+HA-966 injected rats approached but did not reach significance, $t(12)=1.86$, $p=0.087$ (Experiment 4). Also, fear-potentiated startle was significantly lower in rats that received intra-amygdala DCS infusions prior to extinction training compared to rats that received PBS infusions, $t(16)=2.24$ (Experiment 6).

Discussion—Experiments 1-6

The primary finding of these experiments is that DCS, a partial agonist at the strychnine-insensitive glycine-recognition site on the NMDA receptor complex, facilitates extinction of conditioned fear following either systemic injections (Experiments 2, 3, and 4) or intra-amygdala infusions (Experiment 6). Because DCS reduced fear-potentiated startle only in rats that concurrently received extinction training (Experiments 3 and 6), the effects of DCS cannot readily be attributed either to DCS-related neurotoxicity or to anxiolytic drug actions still present 24 hours after drug administration (i.e., during testing). The blockade of DCS's facilitatory influence on extinction by the glycine recognition site antagonist, HA-966, strongly suggests that the effect of DCS was mediated by interactions with the NMDA receptor (Experiment 4). This seems particularly likely insofar as the dose of HA-966 used did not, on it's own, increase fear-potentiated startle. Thus, the ability of HA-966 to reverse DCS effects on extinction cannot be attributed to a summation of independent facilitatory and disruptive effects, mediated by actions on different systems. The failure of either compound to influence fear-potentiated startle when given prior to testing suggests that their effects on extinction reflect direct effects on learning processes rather than on CS-processing or on fear itself.

As indicated earlier, extinction is generally thought to reflect the formation of new inhibitory associations, as opposed to the forgetting of previously formed associations (Pavlov (1927) *Conditioned Reflexes* (University Press, Oxford); Konorski (1948) *Conditioned Reflexes and Neuronal Organization* (University Press, London, Cambridge); Bouton and Bolles (1985) *Context, Event Memories, and Extinction* (Lawrence Erlbaum Associates, Hillsdale, N.J.); Falls and Davis (1995) "Behavioral and Physiological Analysis of Fear Inhibition," in *Neurobiological and Clinical Consequences of Stress: From Normal Adaptation to PTSD*, eds. Friedman et al. (Lippincott-Raven Publishers, Philadelphia); Davis et al. (2000) "Neural Systems Involved in Fear Ihibition: Extinction and Conditioned Inhibition," in *Contemporary Issues in Modeling Psychopathology*, eds. Myslobodsky and Weiner (Kluwer Academic Publishers, Boston); Rescorla (2001) "Experimental Extinction," in *Handbook of Contemporary Learning Theories*, eds. Mowrer and Klein (Erlbaum, Mahwah, N.J.)). Consistent with this view, the evidence to date suggests that the neural mechanisms, neural circuitry, and pharmacology of excitatory fear conditioning and of conditioned fear extinction are similar. For example, systemic administration of the mitogen-activated protein kinase (MAPK) inhibitor, PD98059, as well as intra-amygdala PD98059 infusions, disrupt fear-conditioning as assessed with both freezing (Schafe et al. (2000) *J. Neuroscience* 20:8177-8187) and shock-motivated avoidance learning (Walz et al. (1999) *Behav. Pharmacol.* 10:723-730; Walz et al. (2000) *Neurobiol. Learn. Mem.* 73:11-20) respectively, and intra-amygdala PD98059 infusions also disrupt extinction as assessed with fear-potentiated startle (Lu et al. (2001) *J. Neuroscience* 21:RC162). As previously noted, intra-amygdala AP5 infusions also block fear conditioning as assessed with either fear-potentiated startle or freezing and also block extinction in these same paradigms (Miserendino et al. (1990) *Nature* 345:716-718; Falls et al. (1992) *J. Neuroscience* 12:854-863; Fanselow and Kim (1994) *Behav. Neuroscience* 108:210-212; Maren et al. (1996) *Behav. Neuroscience* 110:1365-1374; Lee and Kim (1998) *J. Neuroscience* 18:8444-8454; Walker and Davis (2000) *Behav. Neuroscience* 114:1019-1033).

Although DCS has previously been shown to enhance learning in a variety of learning paradigms (Monahan et al. (1989) *Pharmacol. Biochem. Behav.* 34:649-653; Flood et al. (1992) *Eur. J. Pharmacol.* 221:249-254; Thompson et al. (1992) *Nature* 359:638-641; Quartermain et al. (1994) *Eur. J. Pharmacol.* 257:7-12; Pitkanen et al. (1995) *Eur. Neuropsychopharmacol.* 5:457-463; Matsuoka and Aigner (1996) *J. Pharmacol. Exp. Ther.* 278:891-897; Pussinen et al. (1997) *Neurobiol. Learn. Mem.* 67:69-74; Land and Riccio (1999) *Neurobiol. Learn. Mem.* 72:158-168), this appears to be the first demonstration of an enhancement of extinction learning by DCS. In fact, Port and Seybold ((1998) *Physiol. Behav.* 64:391-393) reported that DCS retarded extinction of an appetitive instrumental response, and that the NMDA receptor antagonist MK801 enhanced extinction. The latter finding is in contrast to several other results showing that NMDA receptor antagonists disrupt extinction (Falls et al. (1992) *J. Neuroscience* 12:854-863; Cox and Westbrook (1994) *Quarterly J. Exper. Psych.* 47B:187-210; Baker and Azorlosa (1996) *Behav. Neuroscience* 110:618-620; Kehoe et al. (1996) *Psychobiology* 24:127-135; Lee and Kim (1998) *J. Neuroscience* 18:8444-8454). The data used to evaluate extinction in Port and Seybold (1998) *Physiol. Behav.* 64:391-393) were collected while animals were still under the influence of DCS (i.e., within-session extinction), and it is possible that effects on performance obscured effects on extinction. It is also possible, though less likely, that the extinction of instrumental responses responds differently to NMDA receptor manipulations than does the extinction of classically conditioned responses.

Findings implicating amygdala NMDA receptors in both excitatory fear conditioning and conditioned fear extinction are of considerable theoretical interest. Evidence that the extinction of conditioned fear memories might be accelerated by NMDA receptor agonists is also of considerable clinical interest. Many believe that the neural circuitry mediating adaptive fear is closely related if not identical to the neural circuitry mediating clinical fear (e.g., in post-traumatic stress disorder; Rosen and Schulkin (1998) *Psychological Review* 105:325-350, 1998; Bouton et al. (2001) *Psychological Review* 108:4-32; Gorman et al. (2000) *Am. J. Psychiatry* 157:493-505). In clinical populations, a reduced ability to extinguish conditioned fear associations might contribute to the persistence of maladaptive fear and may reduce the effectiveness of therapeutic interventions that rely upon extinction processes (e.g., systematic desensitization, exposure, and imagery therapies). The results reported here suggest that the effectiveness of these traditional clinical approaches might be facilitated by pharmacological interventions that promote extinction. Clinical trials to test this idea are currently being planned.

Experiment 7

Clinical Trial of D-Cycloserine Augmentation of Behavioral Exposure Therapy for Specific Phobia Acrophobia, or fear of heights, has been shown to be responsive to virtual reality exposure (VRE) therapy (Rothbaum et al. (1995) *Am. J. Psychiatry* 152(4):626-628), and VRE therapy has been well validated for different specific phobias and for post-traumatic stress disorder (Rothbaum et al. (1995) *Am. J. Psychiatry* 152(4):626-628; Rothbaum et al. (2000) *J. Consult. Clin. Psych.* 68(6):1020-1026). With VRE for fear of heights, it was shown that there were significant improvements on all outcome measures for the treated as compared to the untreated groups (Rothbaum et al. (1995) *Am. J. Psychiatry* 152(4):626-628). Treated participants in this study reported a positive attitude toward treatment, whereas untreated participants reported negative attitudes. VRE treatment for fear of flying demonstrated that VR treatment was equivalent to standard in vivo exposure therapy, both of which showed significant superiority to waitlist control on all outcome measures (Rothbaum et al. (2000) *J. Consult. Clin. Psych.* 68(6):1020-1026). In these studies, patients appear to improve steadily across sessions as noted by the decrease in subjective discomfort across sessions as would be expected with incremental habituation or extinction to the fearful stimulus.

In this experiment, acute treatment with an NMDA glutamate receptor agonist prior to psychotherapy is used to enhance the effects of VRE therapy. Specifically, an acute dose of D-Cycloserine (DCS) is given to a patient shortly before each individual therapy session over 2 weekly sessions to enhance the final level of VRE treatment efficacy.

Dosing Rationale

DCS has been FDA approved for approximately 20 years, initially for the treatment of tuberculosis, and then as a cognitive enhancer in several clinical trials over the last decade. For tuberculosis, DCS is generally dosed at 500-1000 mg/day divided twice daily (PDR 1997) with chronic treatment. At a dose of 500 mg/day, blood levels of 25-30 mg/ml are generally maintained. The peak blood levels occur within 3-8 hours after dosing, and it is primarily renally excreted with a half-life of 10 hours. Infrequent side effects in patients on chronic dosing schedules (who were generally chronically ill with tuberculosis) include drowsiness, headache, confusion, tremor, vertigo, and memory difficulties, paresthesias, and seizure. Of note, no significant side effects have been reported in any of the clinical studies examining DCS for cognitive enhancement, even when used up to 500 mg/day doses (D'Souza et al. (2000) *Biol. Psych.* 47:450-462; Fakouhi et al. (1995) *J. Geriatri. Psychiatry Neurol.* 8(4):226-230; Randolph et al. (1994) *Alzheimers Dis. Assoc. Disord.* 8(3):198-205; van Berckel et al. (1996) *Biol. Psychiatry* 40(12):1298-1300).

In this experiment, a 50 mg or 500 mg dose of DCS is given to a patient acutely prior to psychotherapy for several reasons. The low dose is based on several clinical trials in which 30-100 mg/day given daily were effective for implicit memory (Schwartz et al. (1996) *Neurology* 46(2):420424) and subscales of dementia rating in Alzheimer's disease (Tsai et al. (1999) *Am. J. Psychiatry* 156(3):467-469). Furthermore 50 mg/day appeared to be most effective in treatment of negative symptoms of Schizophrenia (Goff et al. (1996) *Am. J. Psychiatry* 153(12):1628-1630; Goff et al. (1999) *Arch. Gen. Psych.* 56(1):21-27). The higher dose (500 mg) is chosen because the efficacy of DCS in the lower dose range (10-250 mg/day) has not been effective in several trials by other groups (D'Souza et al. (2000) *Biol. Psych.* 47:450-462; Fakouhi et al. (1995) *J. Geriatri. Psychiatry Neurol.* 8(4): 226-230; Randolph et al. (1994) *Alzheimers Dis. Assoc. Disord.* 8(3):198-205). Using Luteinizing Hormone (LH) secretion as a measure of NMDA receptor activation, it was shown that single doses of 15-150 mg of DCS did not lead to significant increases in LH (van Berckel et al. (1997) *Neuropsychopharm.* 16(5):317-324), but that a single 500 mg dose did effectively stimulate LH release (van Berckel et al. (1998) *Psychopharm.* 138(2):190-197). At this dose, it was noted that there were no changes in cortisol, plasma HVA, or vital sign measures. Furthermore, at this dose there were no reported side effects and no changes in mood scores. Thus it was concluded that single doses as high as 500 mg in an otherwise drug naive, healthy individual would be well tolerated, without side effects, but with clear neuroendocrine effect (van Berckel et al. (1998) *Psychopharm.* 138(2):190-197).

The choice to use DCS in an acute treatment, rather than chronic, format is based on several factors. First is the novel and enormously useful clinical benefit that would be gained from a medication used in a time-limited fashion as an adjunct to psychotherapy. Second, and most importantly, is the issue that there may be significant compensatory changes in the NMDA receptor complex following chronic administration. As with all neurotransmitter receptors, regulation of the NMDA receptor is likely closely controlled for level of activity. Many chronically administered psychotropic agents are thought to function over a prolonged time due to the chronic downregulation of numerous receptor types (reviewed in Ressler and Nemeroff (1999) *Biol. Psychiatry* 46:1219-1233). Most of the extant preclinical data, on which the cognitive enhancement effect of DCS is based, are acute treatment studies in animals (Flood et al. (1992) *Neurosci. Lett.* 146:215-218; Land and Riccio (1999) *Neurobiol. Learn. Mem.* 72:158-168; Matsuoka and Aigner (1996) *J. Pharmacol. Exp. Ther.* 278:891-7). Several of the chronic treatment clinical trials have failed to show efficacy (D'Souza et al. (2000) *Biol. Psych.* 47:450-462; Fakouhi et al. (1995) *J. Geriatri. Psychiatry Neurol.* 8(4):226-230; Randolph et al. (1994) *Alzheimers Dis. Assoc. Disord.* 8(3):198-205). Direct studies in mice of acute versus chronic treatment with DCS suggest that chronic treatment does not enhance learning, whereas acute treatment clearly does (Quartermain et al. (1994) *Eur. J. Pharmacol.* 257(1-2):7-12). Furthermore, the relatively low side effect profile of DCS at chronic doses is almost negligible at acute doses, making acute treatment a safe and low-risk approach to treatment.

Patient Selection

Although the majority of patients with fear of heights are expected to be simply phobic, it is expected that a substantial minority may be agoraphobic. In this experiment, a patient must meet DSM-IV criteria for specific phobia, situational type (i.e., fear of heights) or panic disorder with agoraphobia in which heights are the feared stimulus, or agoraphobia without a history of panic disorder, in which heights are the feared stimulus.

Treatment Schedule

A patient is treated once per week for 2 weeks, with a 50 mg or 500 mg DCS dose administered only on the day of therapy, approximately 4 hours before the initiation of therapy. Thus a patient receives only two doses of medication or placebo total over the 2-week period.

Virtual reality exposure therapy (VRE) is to a series of footbridges over a canyon and a glass elevator that rises 49 floors (Rothbaum et al. (1995) *Am. J. Psychiatry* 152(4):626-628). During VRE sessions the patient wears a head-mounted display with stereo earphones that provides visual and audio cues consistent with being on a footbridge over a canyon or inside a glass elevator. During therapy, the therapist makes appropriate comments and encourages continued exposure until anxiety has habituated.

During each VRE session, anxiety is rated by subjective units of discomfort (SUDs) on a 0 to 100 scale in which 0 indicates no anxiety and 100 indicates panic-level anxiety. Psychophysiological responses (pulse, BP, GSR) are monitored throughout each exposure session.

Assessment

A patient's response to a combination therapy session of DCS and VRE may be assessed using any of the methods listed below. Table 1 shows an assessment schedule for a patient done both before and after the combination therapy.

Assessment Methods a) Interviews

The Initial Screening Questionnaire (Rothbaum et al. (1995) *Am. J. Psychiatry* 152(4):626-628) is a short screening instrument that is used to screen initial phone inquiries to identify those likely meeting study criteria for fear of heights.

The Structured Clinical Interview for the DSM-IV (Spitzer et al. (1987) *Structured Clinical Interview for DSM III-R (SCID)* (New York State Psychiatric Institute, Biometrics Research, New York)) is administered to diagnose and screen for various DSM-III-R axis I disorders (e.g., schizophrenia) as well as establish co-morbid diagnoses.

The Clinical Global Improvement (CGI) Scale is a global measure of change in severity of symptoms. The scale is bipolar with 1=very much improved; 7=very much worse; and 4=no change. It has been used extensively in clinical trials for a variety of psychiatric patients (Guy (1976) *ECDEU Assessment Manual for Psychotherapy* (revised ed., National Institute of Mental Health, Bethesda, Md.)).

b) Self-Report Measures

The Acrophobia Questionnaire (AQ) is a short self-report questionnaire assessing specific symptoms of fear of heights. It is given weekly prior to VRE.

The Attitude Towards Heights Questionnaire (ATHQ) is a separate self-report scale that measures slightly different aspects of avoidance, and other fear of heights related phenomena.

The Rating of Fear Questionnaire (RFQ) (Rothbaum et al. (1995) *Am. J. Psychiatry* 152(4):626-628) is used to further assess level of fear related to heights in general and the VRE therapy.

The State-Trait Anxiety Inventory (STAI; Spielberger et al. (1970) *Manual for the State-Trait Anxiety Inventory (self-evaluation questionnaire)* (Consulting Psychologists Press, Palo Alto, Calif.)) is comprised of 40 items divided evenly between state anxiety and trait anxiety. The authors reported reliability for trait anxiety was 0.81; as expected, figures were lower for state anxiety (0.40). Internal consistency ranges between 0.83 and 0.92.

The Beck Depression Inventory (BDI; Beck et al. (1961) *Archives of Gen. Psych.* 4:561-571) is a 21-item self-report questionnaire assessing numerous symptoms of depression.

The authors report excellent split-half reliability (0.93), and correlations with clinician ratings of depression range between 0.62 and 0.66.

c) Therapist Measure

The subjective units of discomfort (SUDs) is scored by the therapist based on the participant's report during the VRE at 5 minute intervals. SUDS are rated on a 0 to 100 scale in which 0 indicates no anxiety and 100 indicates panic-level anxiety The Behavioral Avoidance Test (BAT) consists of a brief re-exposure to heights via the Virtual Reality environment, in which the therapist assesses the patients subjective level of fear and avoidance of heights.

d) Psychophysiological Measures

Measurement of heart rate (HR) is performed and stored by a non-invasive, computer controlled monitoring device for assessment of autonomic reactivity during VRE.

Measurement of blood pressure (BP) is performed by a non-invasive, computer controlled sphygmomanometer for assessment of vascular tone and autonomic reactivity during VRE Measurement of galvanic skin conductance (GSR) is performed by a non-invasive, computer controlled monitoring device for assessment of autonomic fear responsivity during VRE.

TABLE 1

| Assessment Session | Measures |
| --- | --- |
| Prior to entry | Consent form |
|  | SCID |
| Pre-treatment Assessment | Acrophobia Questionnaire |
|  | Attitude Towards Heights Questionnaire |
|  | Ratings of Fear Questionnaire |
|  | Behavioral Avoidance Test |
|  | BDI |
|  | STAI |
| Weekly VRE Therapy Sessions (x2) | Psychophysiologic measures (HR, BP, GSR) SUDs |
| Post-VRE Assessments and 6 Month Follow up Assessment | Acrophobia Questionnaire |
|  | Attitude Towards Heights Questionnaire |
|  | Ratings of Fear Questionnaire |
|  | CGI |
|  | Behavioral Avoidance Test |

Future Directions

The results presented herein demonstrate that a pharmacologic agent that enhances extinction learning can be administered acutely in combination with a session of psychotherapy, thereby enhancing the effectiveness of the psychotherapy session. The present invention contemplates a variety of specific parameters for such a combination therapy protocol, including the choice of psychotherapy used, the psychiatric disorders to be treated, the particular pharmacologic agent to be used in the methods of the invention, and the timing and dosage of administration of the pharmacologic agent. Particular manifestations of these parameters as contemplated in the present invention are discussed in more detail in the foregoing detailed description of the invention.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the representative embodiments of these concepts presented below.

What is claimed is:

1. A method for treating an individual with a psychiatric disorder, said method comprising administering to the individual in need thereof a therapeutically effective amount of D-cycloserine that enhances extinction learning in combination with a session of psychotherapy, wherein D-cycloserine is administered to the individual only within 24 hours of psychotherapy, and wherein during said session of psychotherapy, said individual is exposed to a stimulus, and trained to develop an altered response to said stimulus.

2. The method of claim 1, wherein said psychiatric disorder is a fear and anxiety disorder, an addictive disorder, and a mood disorder.

3. The method of claim 1, wherein said administration of said therapeutically effective amount of D-cycloserine occurs within about 12 hours before psychotherapy.

4. The method of claim 1, wherein said D-cycloserine is administered at a dose of between about 30-100 mg.

5. The method of claim 1, wherein said D-cycloserine is administered at a dose of between about 400-500 mg.

6. A method for treating a fear and anxiety disorder, said method comprising administering to a patient in need thereof a therapeutically effective amount of D-cycloserine in combination with a session of psychotherapy, wherein D-cycloserine is administered to the patient only within 24 hours of psychotherapy, and wherein during said session of psychotherapy, the patient is exposed to a stimulus, and trained to develop an altered response to said stimulus.

7. The method of claim 6, wherein said administration of said D-cycloserine occurs within about 12 hours before psychotherapy.

8. The method of claim 7, wherein said fear and anxiety disorder is selected from the group consisting of a panic disorder, specific phobia, post-traumatic stress disorder, and an obsessive-compulsive disorder.

9. The method of claim 6, wherein said D-cycloserine is administered at a dose of between about 30-100 mg.

10. The method of claim 6, wherein said D-cycloserine is administered at a dose of between 400-500 mg.

11. A method for treating a fear and anxiety disorder, comprising administering to a patient in need thereof a therapeutically effective amount of d-cycloserine, wherein the administration of d-cycloserine when combined with a session of psychotherapy is more effective in treating the fear disorder or anxiety disorder than a session of psychotherapy alone as measured by an assessment test, wherein D-cycloserine is administered to the patient only within 24 hours of psychotherapy, and wherein during said session of psychotherapy, the patient is exposed to a stimulus, and trained to develop an altered response to said stimulus.

12. The method of claim 11, wherein the d-cycloserine is administered once a week for two weeks.

13. The method of claim 12, wherein the d-cycloserine is administered on a day of a psychotherapy session with the patient.

14. The method of claim 11, wherein the d-cycloserine is administered on a day of a psychotherapy session with the patient.

15. A method of treating a fear and anxiety disorder, comprising:
   a) administering to a patient in need thereof a therapeutically effective amount of d-cycloserine; and
   b) exposing the patient to at least one extinction training event; wherein the D-cycloserine is administered to the patient within 24 hours of an extinction training event; and wherein D-cycloserine is administered to the patient only within 24 hours of an extinction training event.

16. An improved psychotherapy method, wherein the improvement comprises administering to a patient in need thereof a therapeutically effective amount of D-cycloserine that enhances extinction learning when combined with a session of psychotherapy, wherein D-cycloserine is administered to the patient only within 24 hours of psychotherapy, and wherein during said session of psychotherapy, the patient is exposed to a stimulus, and trained to develop an altered response to said stimulus.

* * * * *